United States Patent
Kang

(10) Patent No.: US 10,278,931 B2
(45) Date of Patent: May 7, 2019

(54) COMPOSITION FOR TREATMENT OF INFLAMMATORY BOWEL DISEASE AND ATOPIC DERMATITIS

(71) Applicant: INNOPHARMASCREEN INC., Chungcheongnam-do (KR)

(72) Inventor: In Cheol Kang, Incheon (KR)

(73) Assignee: INNOPHARMASCREEN INC., Chungcheongnam-do (KR)

( * ) Notice: Subject to any disclaimer, the term of this patent is extended or adjusted under 35 U.S.C. 154(b) by 0 days.

(21) Appl. No.: 15/768,374

(22) PCT Filed: Oct. 12, 2016

(86) PCT No.: PCT/KR2016/011434
§ 371 (c)(1),
(2) Date: Apr. 13, 2018

(87) PCT Pub. No.: WO2017/065495
PCT Pub. Date: Apr. 20, 2017

(65) Prior Publication Data
US 2018/0303774 A1 Oct. 25, 2018

(30) Foreign Application Priority Data

Oct. 13, 2015 (KR) .................... 10-2015-0142929
Oct. 11, 2016 (KR) .................... 10-2016-0131313

(51) Int. Cl.
| A61K 31/155 | (2006.01) |
| A61P 17/00 | (2006.01) |
| A61P 1/00 | (2006.01) |
| C07C 279/26 | (2006.01) |
| C07C 317/14 | (2006.01) |
| A61K 31/18 | (2006.01) |
| A61K 31/167 | (2006.01) |
| A23L 33/10 | (2016.01) |
| C07C 233/06 | (2006.01) |

(52) U.S. Cl.
CPC ........... *A61K 31/155* (2013.01); *A23L 33/10* (2016.08); *A61K 31/167* (2013.01); *A61K 31/18* (2013.01); *A61P 1/00* (2018.01); *A61P 17/00* (2018.01); *C07C 233/06* (2013.01); *C07C 279/26* (2013.01); *C07C 317/14* (2013.01); *A23V 2002/00* (2013.01); *C07C 2603/74* (2017.05)

(58) Field of Classification Search
None
See application file for complete search history.

(56) References Cited

U.S. PATENT DOCUMENTS

| 9,133,110 | B2 | 9/2015 | Kim et al. |
| 9,416,098 | B2 | 8/2016 | Kim et al. |
| 9,464,042 | B2 | 10/2016 | Kim et al. |
| 2009/0280069 | A1 | 11/2009 | Godowski |
| 2011/0263901 | A1 | 10/2011 | Sathe et al. |
| 2012/0283299 | A1 | 11/2012 | Kim et al. |
| 2013/0095140 | A1 | 4/2013 | Baron et al. |
| 2017/0114008 | A1 | 4/2017 | Cho et al. |

FOREIGN PATENT DOCUMENTS

| KR | 10-2011-0010763 | 2/2011 |
| WO | WO 2003/037346 | 5/2003 |
| WO | WO 2004/005509 | 1/2004 |
| WO | WO 2011/083998 | 7/2011 |
| WO | WO 2011/083999 | 7/2011 |
| WO | WO 2015/026215 | 2/2015 |
| WO | WO 2016/080810 | 5/2016 |

OTHER PUBLICATIONS

English Translation of Internation Search Report for PCT/KR2016/011343, dated Mar. 17, 2017, WIPO, Korea.

*Primary Examiner* — Brian J Davis
(74) *Attorney, Agent, or Firm* — Rubin and Rudman, LLP

(57) ABSTRACT

The present invention relates to a compound for inhibiting thymic stromal lymphopoietin (TSLP) secretion from mast cells and use thereof. The compound of the present invention was confirmed to significantly inhibit TSLP secretion from mast cells and, accordingly, may be used as a candidate compound for treating and preventing atopic dermatitis, allergic dermatitis, and/or inflammatory bowel disease.

12 Claims, 20 Drawing Sheets

1)

2)

1)

2)

1)

2)

1)

IPS_07001-Cy3
/Control-Cy5

IPS_07001-Cy5
/Control-Cy3

I N R

2)

COMPOSITION FOR TREATMENT OF INFLAMMATORY BOWEL DISEASE AND ATOPIC DERMATITIS

TECHNICAL FIELD

The present invention relates to a compound for inhibiting the secretion of Thymic Stromal Lymphopoietin (TSLP) from mast cells and use thereof for the treatment of inflammatory bowel disease and atopic dermatitis.

BACKGROUND ART

Allergy is a phenomenon in which a living body in contact with an exogenous substance exhibits a response to the substance different from normal responses. When an organism comes into contact with an exogenous substance, an antigen-antibody reaction causes an abrupt change in the body's ability to respond thereto, which is called allergy. For a heterologous substance, the living organism produces antibodies and lymphocytes that specifically react with the antigen, and when the living organism comes into contact the antigen again, it causes various immune responses. This immune response or immune reaction is one of the important defense mechanisms for self-preservation of the living body, and usually acts protectively on the living body, but sometimes this mechanism adversely acts on the living body, thus causing disorders. Allergy means "hypersensitive," and is derived from a Greek word allos, which means "altered." The term "allergy" was first used by the French scholar von Pirque in 1906. Allergy is pronounced in English as al-ler-gi or el-ler-gi and in German as al-le-r-gie, and both are interchangeably used in Korea. Antigens that cause allergic reactions are called allergens, and typical allergens include pollen, drugs, plant fibers, bacteria, food, dyes, chemicals, and the like. The immune system has several defense mechanisms to protect the body against antigens. The most common type of these mechanisms is lymphocytes, which are specified to be in response to specific antigens and include B cells and T cells. B cells bind to an antigen to produce an antibody, which is a protein that destroys and neutralizes the antigen. T cells directly bind to an antigen to thereby stimulate attack, instead of producing an antibody. An allergic reaction occurs as immediate allergy or delayered allergy, and is determined depending on with which of B cells and T cells an antigen reacts. As diseases caused by allergy, there are various diseases including autoimmune diseases, collagen diseases, and the lie, and allergic diseases generally include classical allergic diseases such as anaphylactic shock, food allergy, allergic rhinitis, pollinosis, bronchial asthma, drug allergies, plant allergies, urticaria, eczema, and allergic contact dermatitis. These are allergy-caused diseases, but there are cases in which other in vivo conditions are required for their onset. In addition, same symptoms may be caused by non-allergic mechanisms.

Atopic dermatitis is a chronic, highly recurrent inflammatory skin disease that starts mainly in infancy or childhood, and is accompanied by pruritus (itching), dry skin, and characteristic eczema. In infancy, it starts with eczema on the face and the unfolded parts of the limbs, but characteristically appears as eczema on the bent parts of the arms and the bent parts of back sides of the knees as infants grow. In many cases, atopic dermatitis tends to alleviate naturally as children grow. In adults, lichenification, which is a condition of thickening of the folded skin parts, appears, and many adult cases show eczema on the face, unlike those in childhood. Atopic dermatitis tends to increase globally and the prevalence rate has been reported as 20% of the population.

Despite advanced allergic treatment for allergic patients and a growing increase in sales of excellent allergy therapeutic agents, allergic symptoms of people have become severe and the number of allergic patients is increasing rapidly.

These are attributable to limitations of existing therapeutic agents including the amplification of allergic diseases via various other routes, temporary improvement effects, and the like.

Existing atopic dermatitis therapeutic agents alleviate pruritus and restore damaged skin surface, and are mostly immunosuppressants or steroid agents which are recognized to have side effects.

Therefore, there is a need to develop a therapeutic agent capable of treating atopy as immune hypersensitivity by addressing fundamental causes of atopy in atopy treatment, unlike immunosuppressants or steroid agents which have previously been reported to have side effects.

Meanwhile, inflammatory bowel disease (IBD) is classified into two diseases: ulcerative colitis and Crohn's disease, which are clinically similar but different from each other in histological, endoscopic, and immunological aspects, and the activation of inflammatory cells is known to be an important etiology of IBD. Continuous or improper activation of the intestinal immune system plays an important role in the pathophysiology of chronic mucosal inflammation, and in particular, the infiltration of neutrophils, macrophages, lymphocytes, and mast cells eventually results in mucosal destruction and ulceration. Infiltered and activated neutrophils lead to generation of reactive oxygen species and reactive nitrogen species, and these active species are cytotoxic substances that induce cellular oxidative stress by crosslinked proteins, lipids, and nucleic acids and cause epithelial dysfunction and damage.

When an inflammatory disease occurs, a variety of inflammatory cytokines are secreted in the mucosa of the intestinal tract. TNF-α is highly expressed in colonic lumens and colonic epithelial cells in patients with ulcerative colitis. According to recent studies, it has been known that TNF-α plays an important role in the pathogenesis of ulcerative colitis. Infliximab, which is an anti-TNF-α antibody, has been known to be effective not only in the treatment of boils, but also in the treatment of previously untreated Crohn's disease. However, such therapies are costly and, in some patients, cause side effects such as fluid responses or infectious complications.

Currently, 5-aminosalicylic acid (5-ASA)-based drugs that block the production of prostaglandins, for example, sulfasalazine and the like, or immunosuppresants such as steroids are used as therapeutic agents for inflammatory bowel disease.

Sulfasalazine is prone to cause side effects or adverse effects such as abdominal fullness, headache, rash, liver disease, leukopenia, agranulocytosis, male infertility, and the like. In addition, it is unclear whether sulfasalazine has a sufficient effect of inhibiting recurrence in patients with the affected part of the intestine incised or patients showing improvement.

Steroid immunosuppressants are adrenocortical steroids, which may show short-term effects but cannot improve the long-term prognosis and have limitations in being used only in acute cases due to side effects such as induced infectious diseases, secondary adrenocortical insufficiency, peptic ulcer, diabetes, mental disorder, and steroid kidney disease.

Thus, there have not yet been reliable therapeutics for inflammatory bowel disease, and therefore, there is a need to develop an effective therapeutic agent therefor.

PRIOR ART REFERENCE

Korean Patent Publication No. 1020100058104.

DISCLOSURE

Technical Problem

The present invention has been made in view of the above-described problems, and it is an object of the present invention is to provide a novel candidate material for treating allergic atopic dermatitis.

It is a further object of the present invention to provide a novel candidate material for treating inflammatory bowel disease.

Technical Solution

To achieve the above objects, the present invention provides one compound selected from compounds represented by Formulae 1 to 4 below or a pharmaceutically acceptable salt thereof.

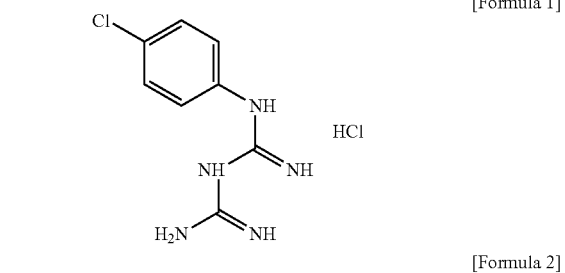

[Formula 1]

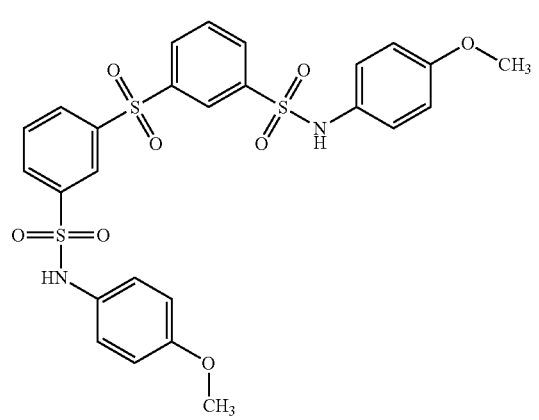 [SMILES: COc1ccc(NS(=O)(=O)c2cccc(S(=O)(=O)c3cccc(S(=O)(=O)Nc4ccc(OC)cc4)c3)c2)cc1]

[Formula 2]

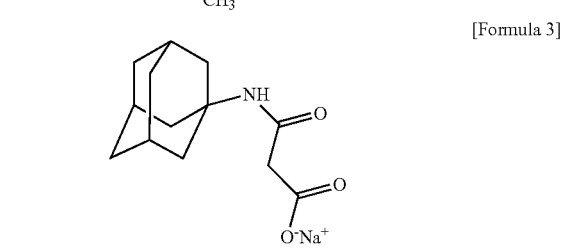

[Formula 3]

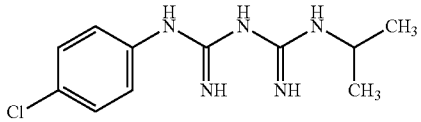

[Formula 4]

In one embodiment of the present invention, the compounds may inhibit the secretion of thymic stromal lymphopoietin (TSLP) from mast cells, but is not limited thereto.

In another embodiment of the present invention, the compounds may be effective in treating atopic dermatitis, but the present invention is not limited thereto.

In another embodiment of the present invention, the compounds may be effective in treating inflammatory bowel disease, but the present invention is not limited thereto.

The pharmaceutically acceptable salts of the present invention include salts derived from inorganic bases such as lithium (Li), sodium (Na), potassium (K), calcium (Ca), magnesium (Mg), iron (Fe), copper (Cu), zinc (Zn), and manganese (Mn); salts of organic bases such as N,N'-diacetyl ethylenediamine, glucamine, triethylamine, chlorine, hydroxide, dicyclohexylamine, metformin, benzylamine, trialkylamine, thiamine, and equivalents thereof; chiral bases such as alkylphenylamine, glycinol, phenyl glycinol and equivalents thereof; natural amino acid salts such as glycine, alanine, valine, leucine, isoleucine, norleucine, tyrosine, cystine, cysteine, methionine, proline, hydroxyl proline, histidine, ornithine, lysine, arginine, serine, and equivalents thereof; quaternary ammonium salts of compounds of the present invention having an alkyl sulfate such as an alkyl halide, MeI, and $(Me)_2SO_4$ and equivalents thereof; artificial amino acids such as D-isomer, substituted amino acid, or the like; guanidine, guanine substituted with one selected from nitro, amino, alkyl, alkenyl, and alkynyl, ammonium or substituted ammonium salts, and aluminum salts. Salts may include acid-added salts, and examples of suitable salts include sulphates, nitrates, phosphates, perchlorates, borates, hydrohalides, acetates, tartrates, maliates, citrates, fumarates, succinates, palmoates, methanesulfonate, benzoate, salicylate, benzenesulfonate, ascorbate, glycerophosphate, ketoglutarate, and equivalents thereof. Pharmaceutically acceptable solvent compounds include crystallization solvents such as hydroxides or alcohols.

The present invention also provides a pharmaceutical composition for preventing and treating atopic dermatitis, comprising the compound of the present invention as an active ingredient.

The present invention also provides a pharmaceutical composition for preventing and treating allergies, comprising the compound of the present invention as an active ingredient.

The present invention also provides a pharmaceutical composition for treating inflammatory bowel disease, comprising the compound of the present invention as an active ingredient.

Single unit dosage forms of the present invention may be administered to a patient orally, intramucosally (e.g., nasally, sublingually, vaginally, orally, or rectally), parenterally (e.g., subcutaneously, intravenously, bolus injection, intramuscularly, or intraarterially), or transdermally. Examples of dosage forms include, but are not limited to, tablets; caplets; capsules such as soft elastic gelatin capsules; cachets; troches; lozenges; dispersions; suppositories;

ointments; wetting agents (cataplasia); pastes; powder; dressing; creams; plaster; solutions; patches; aerosols (e.g., nasal sprays or inhalers); gels; suspensions (e.g., aqueous or non-aqueous liquid suspensions, oil-in-water liquid emulsions, or water-in-oil liquid emulsions, solutions, and liquid preparations suitable for oral administration or mucosal administration to a patient which include elixir; liquid preparations suitable for parenteral administration and sterile solid preparations that can be processed into liquid dosage forms suitable for parenteral administration (e.g., crystals and non-crystalline solids).

The composition, shape, and type of dosage form of the present invention may typically vary according to applications thereof. For example, a dosage form suitable for mucosal administration may include a smaller amount of the active ingredient than that in a dosage form suitable for oral administration used in treating the same disease. These aspects of the present invention will be fairly apparent to those of ordinary skill in the art (reference: Remington's Pharmaceutical Sciences (1990) 18th ed., Mack Publishing, Easton Pa.).

Typical pharmaceutical compositions and dosage forms include one or more excipients. Suitable excipients are apparent to those of ordinary skill in the pharmaceutical art, and the present invention is not limited to examples of suitable excipients described herein.

Whether a particular excipient is suitable for a pharmaceutical composition or a dosage form depends on various factors well known in the art, including methods of formulating preparations to be administered to a patient, but is not limited thereto. For example, dosage forms for oral administration such as tablets may include an excipient not suitable for use in preparations for non-oral administration.

The suitability of a particular excipient may also depend on a particular active ingredient of the dosage form. For example, the decomposition of certain active ingredients may be accelerated by an excipient such as lactose or by exposure to an aqueous solution. Active ingredients, including primary or secondary amines (e.g., N-desmethylvenlafaxine and N, N-didesmethylvenlafaxine) are particularly sensitive to such accelerated decomposition.

The present invention also provides pharmaceutical composition and dosage form that include one or more compounds that reduce a decomposition rate of the active ingredient. These compounds include, but are not limited to, antioxidants such as ascorbic acid, pH buffer solutions, and salt buffer solutions.

Similar to the amount and type of excipient, the amount and type of active ingredient in the dosage form may vary according to factors such as a method of administration to a patient, but the present invention is not limited thereto. However, a typical dosage form of the present invention includes the compound of the present invention or a pharmaceutically acceptable salt thereof in an amount ranging from about 1 mg to about 1,000 mg, preferably, about 50 mg to about 500 mg, and most preferably, about 75 mg to about 350 mg. Determination of a suitable dosage or dosage form for a particular patient is within the scope of the art to which the present invention pertains.

The present invention also provides a cosmetic composition for alleviating and relieving atopic dermatitis, comprising the compound of the present invention as an active ingredient.

The present invention also provides a cosmetic composition for alleviating and relieving allergies, which includes the compound of the present invention as an active ingredient.

The cosmetic composition of the present invention may be prepared in various forms, for example, emulsions, lotions, creams (oil-in-water type, water-in-oil type, multiphase), solutions, suspensions (anhydrous and aqueous), anhydrous products (oil and glycols), gels, masks, packs, powder, and the like.

The present invention also provides a food composition for alleviating and relieving atopic dermatitis, comprising the compound of the present invention as an active ingredient.

The present invention also provides a food composition for alleviating and relieving allergies, which includes the compound of the present invention as an active ingredient.

Effects of the Invention

As is apparent from the foregoing description of the present invention, compounds of the present invention have been found to significantly inhibit TSLP secretion from mast cells, and, accordingly, can be used as candidate materials for treating and preventing atopic dermatitis and/or allergic dermatitis and inflammatory bowel disease.

EXAMPLES

Figure 1:
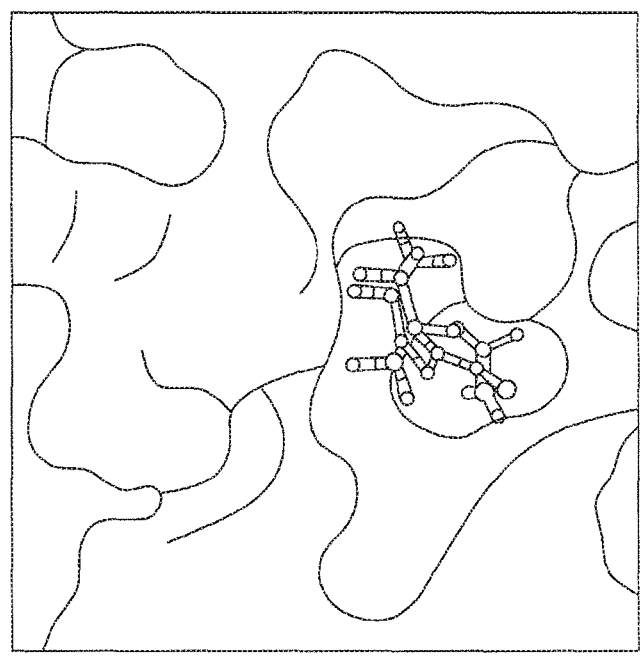
FIG. 1 shows docking results of caspase-1 and ChemBridge library compounds.

Hereinafter, the present invention will be described in further detail with reference to the following non-limiting examples. However, these examples are provided for illustrative purposes only and are not intended to limit the scope of the present invention.

Example 1

Discovery of Therapeutic Candidate Materials Structure-Based in-Silico Screening Using CADD Technology A. Experimental method: To perform in-silico screening on caspase-1 target protein, a computer-assisted molecular docking simulation was conducted.

(1) Protein preparation: A Protein Data Bank (PDB) caspase-1 structure (PDB id 2HBQ) was used as an initial structure of the target protein, and a modeling software was used to supplement missing hydrogen atoms and remove non-crystal water molecules, thereby completing a molecule model of the target protein. The completed protein model was stabilized via energy minimization and then used for simulation.

(2) Ligand preparation: Of the compound libraries, 636,565 compounds of ChemBridge were subjected to salt removal and ionization using a Ligprep module.

(3) Receptor grid generation: The docking site was limited to 30 boxes near the binding site of 3-[2-(2-benzyloxycarbonylamino-3-methyl-butyrylamino)-propionylamino]-4-oxo-pentanoic acid (z-VAD-FMK). The software used for calculation is a Glide program available from Schrodinger. A Glide function was used as a scoring function, and Glide scores for final results were obtained.

(4) Ligand docking: A maximum of 10 docked poses for each ligand compound were calculated, results were obtained in a descending order of scores, and an output file was obtained. Structure searching was performed in a Glide-SP mode to obtain results for the compounds in an order from the highest to the lowest final scores that were corrected as a result of docking calculation.

Example 2

Study of Efficacy of Active Ingredient on Regulation of Atopy-Rlated Factor in in Vitro Model of Allergic Atopic Dermatitis Analysis of Allergy Inhibitory Activity of In Vitro Cell-Based Candidate Materials A. Experimental Method (1) Cell culture: A human mast cell line (HMC-1) was cultured in an IMDM supplemented with 10% FBS at 37° C. and 5% $CO_2$. Candidate materials were dissolved in DMSO, and then filtered using a 0.22 μm filter. The resulting candidate materials were diluted with DMSO and the HMC-1 cells were treated therewith.

(2) Cytotoxicity (MTT-assay): Mast cells ($3 \times 10^5$ cells/ml) were stabilized for 1 hour and then treated with 10 μM candidate materials, followed by treatment with PMA and A23187 (PMACI), and then cultured for 8 hours. After culturing, the medium was replaced by a fresh medium, 5 mg/ml of an MTT solution was then added thereto, and the mast cells were incubated at 37° C. for 4 hours. 250 DMSO was added to the mast cells, MTT formazan was extracted therefrom, and absorbance of each well was measured at 540 nm using an ELISA reader.

(3) Enzyme-linked immunosorbent assay (ELISA): Mast cells ($3 \times 10^6$ cells/ml) were stabilized for 1 hour, and then treated with 0.1 μM, 1 μM, and 10 μM of candidate materials, followed by treatment with PMACI for 8 hours. The mast cells were centrifuged to obtain supernatants. To measure the amount of TSLP secreted from the cells, ELISA was used. The ELISA was performed in 96-well plates coated with 1 μg/well of TSLP capture Ab. The coated plates were washed twice with PBS. The cells were treated with PBS containing 10% FBS for 2 hours. Thereafter, the cells were washed with PBS containing 0.05% Tween-20 (Sigma), and recombinant TSLP was used to draw a standard curve. Subsequently, the plates were exposed to a biotinylated-TSLP antibody, Avidin peroxidase, an ARTS substrate containing 30% $H_2O_2$, and then measured at 405 nm.

(4) Caspase-1 assay: Recombinant caspase-1 and a drug were allowed to react, and then activity measurement was performed using a caspase-1 assay kit (R&D Systems Inc., Minneapolis, Minn., USA).

(5) Reverse transcription-polymerase chain reaction (RT-PCR) quantitative real time PCR: Total RNA was isolated from cells and tissues, and cDNA was synthesized using a reverse transcriptase and was then reacted with cytokine primers to be analyzed, followed by PCR and real-time PCR. The RT-PCR products were subjected to electrophoresis using 1.5% agarose gel for analysis.

(6) Western blotting analysis: Cells were seeded in a 6-well plate and then treated with a drug, and after a certain period of time, the cells were harvested. After harvest, the cells were washed with PBS and then lysed. 50 μg of tissue protein and cell extract protein were subjected to electrophoresis on 12% gel, transferred to nitrocellulose paper, and then blocked with 6% bovine serum albumin for 2 hours. Each protein was reacted with a primary antibody overnight and washed with PBS-tween. Thereafter, the resulting protein was reacted with a secondary antibody for 2 hours, washed, and then detected using an ECL solution kit.

(7) Statistical analysis: Experimental results were obtained by performing at least three experiments and an average thereof was recorded, and analysis was performed using SPSS ver 11.5. Statistical significance was compared between the treated groups and compared by ANOVA along with independent t-test and Tukey's posthoctest, and results of $P<0.05$ were considered statistically significant.

Example 3

Construction of in Vivo Experiment

Experimental Method

A. Experimental animal: 5-week-old male BALB/c mice obtained from. Daehan Biolink (Eumseong, Chungbuk) were adapted for 2 weeks in a clean animal breeding room (small animal room #2-302) at Hoseo University Safety Evaluation Center, set under environmental conditions: temperature of 22±3° C.; relative humidity of 50±20%; ventilation frequency of 10 to 15 times/hour, illumination for 12 hours; and illuminance of 150 Lux to 300 Lux, and then used in an experiment.

4 experimental animals were accommodated in each of polycarbonate cages (270×500×200 mm, KYERYONG SCIENCE). Feed (5053-Picolab Rodent 20, PMI Nutrition International) and drinking water (ultraviolet sterilized filtered water) were allowed to ingest freely. All procedures of the experiment were conducted after approved by the Ethics Committee of the Hoseo University Safety Evaluation Center (HTRC-15-19).

B. Dermatitis induction: Hairs on the back of each mouse were removed and maintained for 24 hours, and then 150 μl of a 1% 2,4-dinitrochlorobenzene(DNCB) solution (acetone: olive oil=3:1) was applied on the hair-removed site once a week for 3 weeks. After week 3, the DNCB solution was applied on the site twice a week for 3 weeks to induce atopic dermatitis.

C. Treatment: Mice were divided into 6 groups, and 0.5% DMSO was applied on animals as a control and 200 μl of each of 0.01 μM, 0.1 μM, and 1 μM test material was applied on animals as experimental groups for 3 weeks. 50 μl of 0.1% dexamethasone dissolved in a crude alcohol was applied on animals as a positive control at intervals of 2 days.

TABLE 1

| Experimental Groups | Test material | Number of animals | Treatment concentration |
| --- | --- | --- | --- |
| Group 1 | Control (0.5% DMSO) | 6 | 0 |
| Group 2 | DNCB | 6 | 0 |
| Group 3 | DNCB + Dexamethasone | 6 | 0.1% |
| Group 4 | DNCB + test material | 6 | 0.01 μM |
| Group 5 | DNCB + test material | 6 | 0.1 μM |
| Group 6 | DNCB + test material | 6 | 1 μM |

D. Biopsy: After application of the test material was completed, the dorsal skin of each experimental animal was incised under heart anesthesia, some of them were rapidly frozen using liquid nitrogen and stored at −70° C. before analysis, and the remainder was fixed with 10% neutral buffered formalin for 24 hours. The fixed tissues were prepared into slides through general tissue processing, and then subjected to hematoxylin & eosin (H&E) staining to measure the thickness of the epidermal layer. In addition, toluidine blue staining was performed to observe a quantitative change of mast cells. While the stained tissues were observed by an optical microscope, the thickness of the epidermal layer and the number of mast cells were obtained using an image analyzer (Olympus DP-21).

E. IgE level measurement: IgE concentration in blood was measured by (SHIBAYAGI, Japan) using serum collected when autopsy was performed. 50 μL of an IgE standard solution and the sample were placed in antibody-attached 96 wells and allowed to react for 2 hours, and then 50 μL of a biotin-conjugated anti-IgE antibody solution was added to each well and allowed to react for 2 hours. Thereafter, the resulting sample was reacted with a HRP-avidin solution for 1 hour and a chromogenic substrate (TBM) reagent for 20 minutes, and the reaction was stopped using a reaction stopper. Absorbance of the sample was measured at 450 nm using ELISA (Molecular devices Emax).

Example 4

Acute Dermal Toxicity Test

Experimental Method

A. Breeding Environment (1) Environmental Conditions: In the present experiment, experimental animals were bred in a clean animal breeding room (small animal room #2-302) at Hoseo University Safety Evaluation Center, set under environmental conditions: temperature of 22±3° C.; relative humidity of 50±20%; ventilation frequency of 10 to 15 times/hour; illumination period of 12 hours; and illuminance of 150 Lux to 300 Lux.

(2) Cages and rugs: Two or three animals per sex were accommodated in each of polycarbonate cages (270×500×200 mm, KYERYONG SCIENCE) with a stainless steel mesh lid during an acclimation period, and after group division, 1 animal per sex was accommodated therein. As the rugs, sterile betachips (NEPCO) irradiated with gamma rays were used.

(3) Feed and drinking water: The animals were fed freely a mouse feed for laboratory, animals (5053-Picolab Rodent 20) manufactured by PMI Nutrition International, and filtered water treated with ultraviolet sterilization (R/O water) was freely supplied as drinking water.

(4) Examination of contaminant in feed and drinking water: Contaminants in the feed were examined by receiving a test result from the feed manufacturer, and the quality of drinking water was checked for contamination by regular inspection according to the corresponding SOP of the present test institute and it was confirmed that there were no contaminants.

B. Test Method (1) Composition of Experimental Groups

TABLE 2

| Experimental Groups | Test material | Sex | Animal No. (heads) | Dose (μM/kg/4 ml bw) |
|---|---|---|---|---|
| Group 1 | IPS-07001 | male | 1101 to 1105 (5) | 0 |
| | | female | 2101 to 2105 (5) | |
| Group 2 | | male | 1206 to 1210 (5) | 200 |
| | | female | 2206 to 2210 (5) | |

(2) Administration:

TABLE 3

| Administration route and reason for selection | Percutaneous administration was selected according to request of test client |
|---|---|
| Number of administration | Once a day, exposure for 24 hours after single administration |
| Dosage calculation | Dosage (mg/kg) was calculated on the basis of body weight on the day of administration |

(3) Experimental Method (A) About 24 hours before administration, hairs on the dorsal part was removed such that the hair-removed site accounted for about 10% or more of the entire surface area thereof, and attention was paid not to injure the skin.

(B) On the day of administration, a dosage for each individual was calculated, and then a test material was sufficiently wetted with a solvent and then applied on the site corresponding to about 10% (about 44 cm) of the entire surface area.

(C) The test material was kept in contact with the skin using a porous gauze, a non-irritating tape, and a bandage during the 24-hour exposure period.

(D) When the exposure period was terminated, the remaining test material was removed using tepid water.

(4) Observation Items (A) General symptom observation: All animals were observed intensively from 30 minutes to 4 hours after administration, and general symptoms were observed once a day for 14 days. At the time of observation, death and clinical symptoms were recorded on an individual basis.

(B) Body weight measurement: All animals were measured at the time of receipt, at the time of group division, immediately before administration (day of administration), and on day 1, day 4, day 7, day 10, and day 14 after initiation of administration.

(C) Autopsy: During the test, dead animals were immediately autopsied and organs were inspected with the naked eye, and at the end of the test, all living animals were euthanized by $CO_2$ gas inhalation and venesectioned, and then the organs visually examined.

(D) Lethal dose (LD50) calculation: Since no mortality was observed in the dosage of this test, the lethal dose (LD50) was not calculated.

(E) Statistical analysis: Body weight data were expressed as mean and standard deviation, and no statistical analysis of body weight was performed.

Example 5

Construction of Antibody Microarray System

Experimental Method

A. Preparation of tissue samples: The mouse skin tissue was frozen in liquid nitrogen and then finely ground in a mortar. Liquid nitrogen was intermittently added to prevent the tissue from being thawed. The finely ground skin tissue was placed in lysis M buffer to prepare a tissue sample lysate.

B. Fluorescent labeling of tissue lysates: Proteins were extracted from each of the tissue lysate treated with the sample for a certain period of time and an untreated tissue lysate (Lysis M extraction solution, Roche) and labeled with a fluorescent material (Cy3 or Cy5) (GE Healthcare). First, the amount of protein from each tissue lysate was adjusted to be at least 1 mg, and then coupling buffer (0.1M sodium carbonate buffer, pH 9.3) was added and mixed well. Cy3 and Cy5 dyes were added to each tissue lysate to which the coupling buffer had been added and mixed well for labeling at 4° C. for 16 hours. A control treated only with DNCB was labeled with Cy3 and Cy5, and the experimental groups treated with the sample were also labeled with Cy3 and Cy5. After labeling with the fluorescent dyes, free dyes were removed using a Post-reactive Spin column (Sigma).

C. Fabrication of antibody microarrays: ProteoChip™ (Proteogen, Inc., Seoul, Korea) was used as a protein chip, and antibody microarrays were fabricated by spotting antibodies against 26 proteins in cells on a substrate immobilized with 200 μg/ml of protein A on the ProteoChip™. First, the antibodies were diluted to 100 μg/ml with phosphate buffer containing 30% glycerol and the antibody arrays were fixed overnight at 4° C. The antibody chip was washed three times with PBST and blocked with 3% BSA in a stirrer at room temperature for 1 hour. After blocking, the chip was washed with PBST solution (phosphate buffer containing 0.05% Tween 20) to remove excess BSA and dried with $N_2$ gas.

D. Hybridization of antibody arrays: Tissue lysates labeled with fluorescent materials were quantified (Bradford method), and 30 μg of each fluorescently labeled samples were mixed in 10 ml of a reaction solution. The antibody chip was immersed in the buffer in which the fluorescently labeled sample was placed to allow a reaction to occur at 30° C. for 1 hour. After the reaction, the antibody chip was washed twice with PBST solution and dried with nitrogen gas. Each slide was analyzed using a fluorescent microarray scanner. Scanning was performed after adjusting PMT values so that main peaks of Cy3 and Cy5 were about 10,000. The ratio of Cy5 to Cy3 in each spot was calculated using a software (Genepix 6.0). The INR values were calculated by sample-Cy5/control-Cy3×sample-Cy3/control-Cy5. If there is no difference in expression, the ideal INR value is 1, values of 1 or more mean an increase in expression, and values less than 1 mean a decrease in expression.

E. Western blotting analysis: Western blotting analysis was performed to verify differences in protein expression in the above antibody array experiment. Proteins from the tissue lysates were separated on SDS-PAGE. The electrophoresed proteins were then transferred onto the PVDF membranes. After washing with PBST solution, the PVDF membranes were blocked with 5% skim milk powder for 1 hour and then reacted with a primary antibody overnight at 4° C. The membranes were washed with PBST solution and reacted with a secondary antibody (anti-IgG) conjugated with horseradish peroxidase (HRP) for 1 hour at room temperature and examined with a photoresist film.

Results of the above example will be described below.

Structure-Based in-Silico Screening Using CADD Technology

Results for 50 compounds with the highest final score corrected as a result of docking calculation were obtained, and molecular structures thereof were shown in tables.

A. The score results of the compounds are shown in Tables below.
TABLE 4
|    | ID      | Score    | ID      | Score    | ID      | Score    |
|----|---------|----------|---------|----------|---------|----------|
| 1  | 5173488 | −8.25902 | 7249234 | −7.19073 | 7936732 | −7.03225 |
| 2  | 5572011 | −8.10539 | 5541710 | −7.18264 | 6589632 | −7.02742 |
| 3  | 5116307 | −8.09505 | 5182410 | −7.13911 | 7579578 | −7.02315 |
| 4  | 5173962 | −7.83898 | 5119461 | −7.12365 | 7270409 | −6.98396 |
| 5  | 7663208 | −7.75609 | 5182436 | −7.12115 | 7290917 | −6.94433 |
| 6  | 5356744 | −7.49706 | 7808944 | −7.10769 | 5566788 | −6.9397  |
| 7  | 5117545 | −7.44377 | 5916129 | −7.09631 | 6181266 | −6.91605 |
| 8  | 5116232 | −7.3576  | 5248955 | −7.08261 | 7933953 | −6.9136  |
| 9  | 7231009 | −7.31524 | 9198688 | −7.0455  | 5808421 | −6.90651 |
| 10 | 7894092 | −7.21013 | 9150101 | −7.03455 | 5535147 | −6.89749 |
TABLE 5
|    | ID      | Score    | ID      | Score    |
|----|---------|----------|---------|----------|
| 1  | 7123737 | −6.89518 | 9138070 | −6.80033 |
| 2  | 7940511 | −6.86224 | 9030779 | −6.79826 |
| 3  | 5173510 | −6.85642 | 7967935 | −6.79613 |
| 4  | 5211084 | −6.85482 | 5235245 | −6.79222 |
| 5  | 7238182 | −6.85347 | 9141139 | −6.78522 |
| 6  | 9339450 | −6.83857 | 9143017 | −6.77679 |
| 7  | 6392971 | −6.8121  | 7933471 | −6.77184 |
| 8  | 4031614 | −6.80955 | 7271310 | −6.75385 |
| 9  | 5554416 | −6.80617 | 7934027 | −6.74975 |
| 10 | 7247002 | −6.80133 | 7614505 | −6.74535 |
B. Information on structures of the compounds are shown in Table below.
TABLE 6
| 構造 | ID |
|------|----|
| 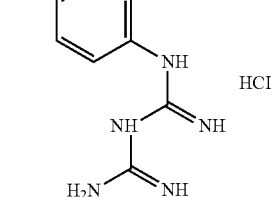 | 5182436 |
| 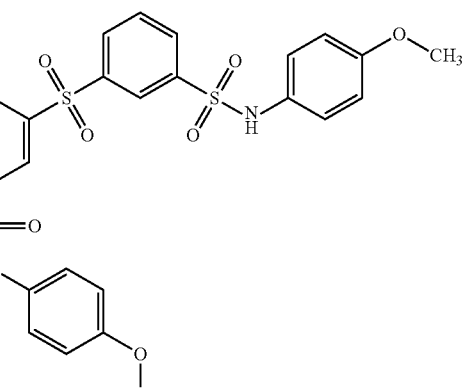 | 5211084 |
| 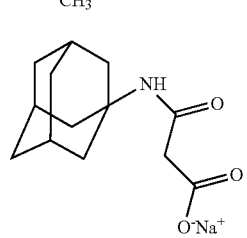 | 5356744 |

In Vitro Cell-Based Analysis of Allergy Inhibitory Activity of Candidate Materials A. Screening of Regulators of Atopic Dermatitis Causative Agent TSLP.

Caspase-1 induces the secretion of TSLP, which is an atopic dermatitis causative agent. To explore TSLP regulatory substances, mast cells, which are causative cells of atopic dermatitis, were stimulated with PKC activator PMA and calcium ionophore A23187 (PMACI). TSLP secretion from the stimulated mast cells was found to significantly increase compared to that from unstimulated cells (Blank), and the effects of various candidate materials were examined. As a result, it was found that 5182436, 5211084, and 5356744 substances significantly inhibited TSLP secretion from mast cells (see FIG. 2).

B. Verification of Cytotoxicity of TSLP Regulating Substances

Figure 3:
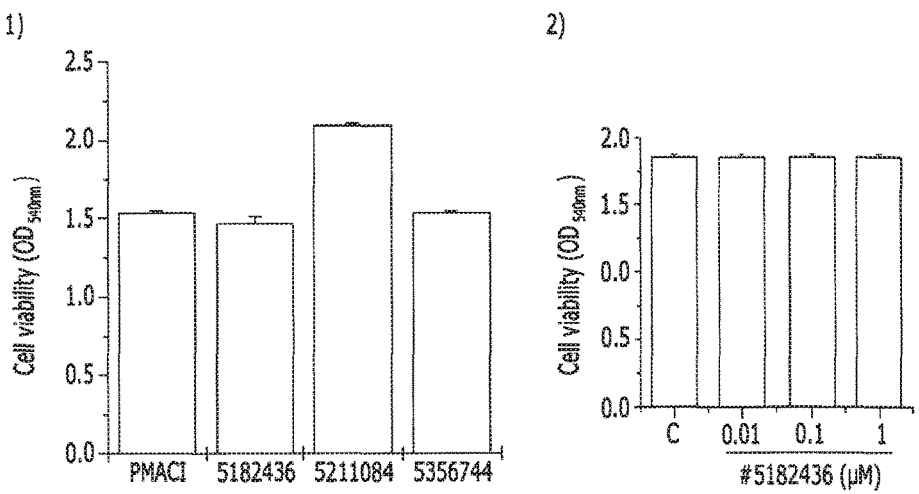
FIG. 3 shows cytotoxicity measurement results in HMC-1 cells.

To examine cytotoxicity of effective materials, MTT-assay was performed, and the MTT-assay results showed that IPS-07002(5211084) and IPS-07003(5356744) did not exhibit cytotoxicity at a concentration of 10 μM. However, it was confirmed that IPS-07001 (5182436) exhibited cytotoxicity at a concentration of 10 μM. As a result of repeatedly performing experiments at various concentrations, IPS-07001(5182436) exhibited no cytotoxicity up to 1 μM (see FIG. 3).

Figure 4:
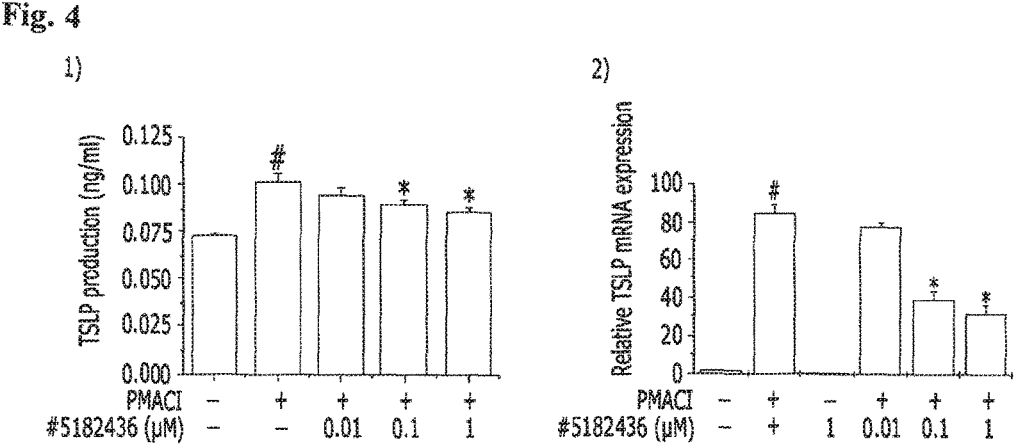
FIG. 4 shows measurement results of TSLP and mRNA expression in HMC-1 cells by IPS-07001(5182436): 1) measurements of the amount of TSLP by IPS-07001, and 2) measurements of mRNA expression by IPS-07001.

C. Repeated Experiments for Effect of IPS-07001 (5182436) on Regulation of TSLP Production Repeated experiments were conducted to examine the effect of IPS-07001 on regulation of TSLP production at non-cytotoxic concentrations, and from the repeated experiment results, it was confirmed that IPS-07001 significantly regulated TSLP production at a concentration of 0.011 μM. IPS-07001 also significantly inhibited TSLP mRNA expression (see FIG. 4).

D. Analysis of Effect of IPS-07001(5182436) on Regulation of Caspase-1 Activity

Figure 5:
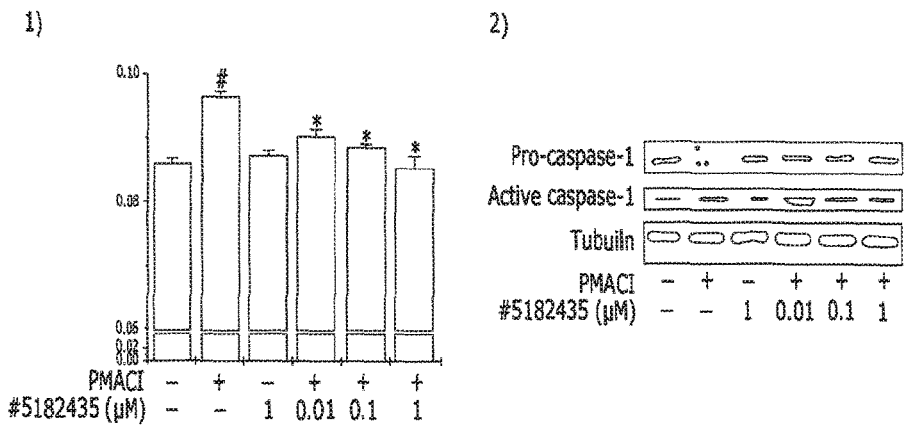
FIG. 5 shows measurement results of caspase-1 activity in HMC-1 cells by IPS-07001(5182436):1) measurements of the effect of IPS-07001 on caspase-1 activity, and 2) changes in caspase-1 expression by the activity of IPS-07001 by western blotting.

To investigate the regulatory effect of #5182436 on caspase-1 activity, a caspase-1 assay was conducted using cell extracts. As a result, it was found that IPS-07001 significantly inhibited caspase-1 activity in a concentration-dependent manner. In addition, it was found that IPS-07001 inhibited the expression of active caspase-1 (see FIG. 5).

Figure 6:
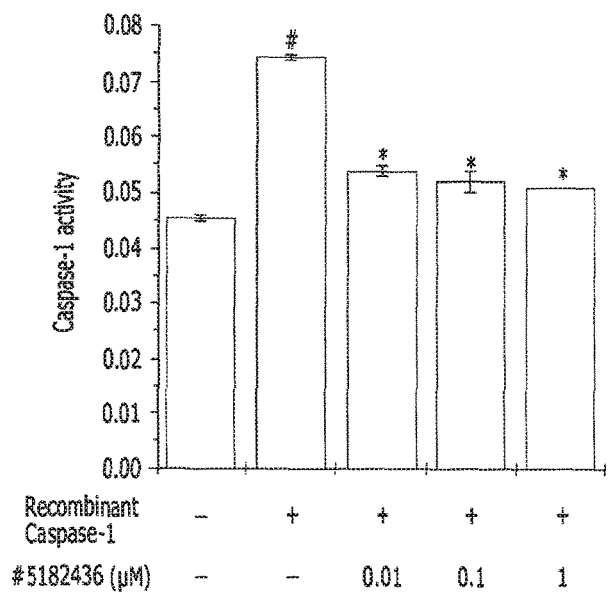
FIG. 6 shows measurement results of the inhibitory effect of IPS-07001(#5182436) on caspase-1 activity.

E. Kinetic Assay-Based Verification of Regulatory Effect of IPS-07001(5182436) on Caspase-1 Activity To investigate the regulatory effect of IPS-07001 on caspase-1 activity, a caspase-1 assay was conducted. As a result, it was found that IPS-07001 significantly inhibited caspase-1 activity in a concentration-dependent manner (see FIG. 6).

F. Experiment for Regulatory Effect of #5182436 on Inflammatory Cytokine Production in Human Mast Cells (HMC-1).

Figure 7:
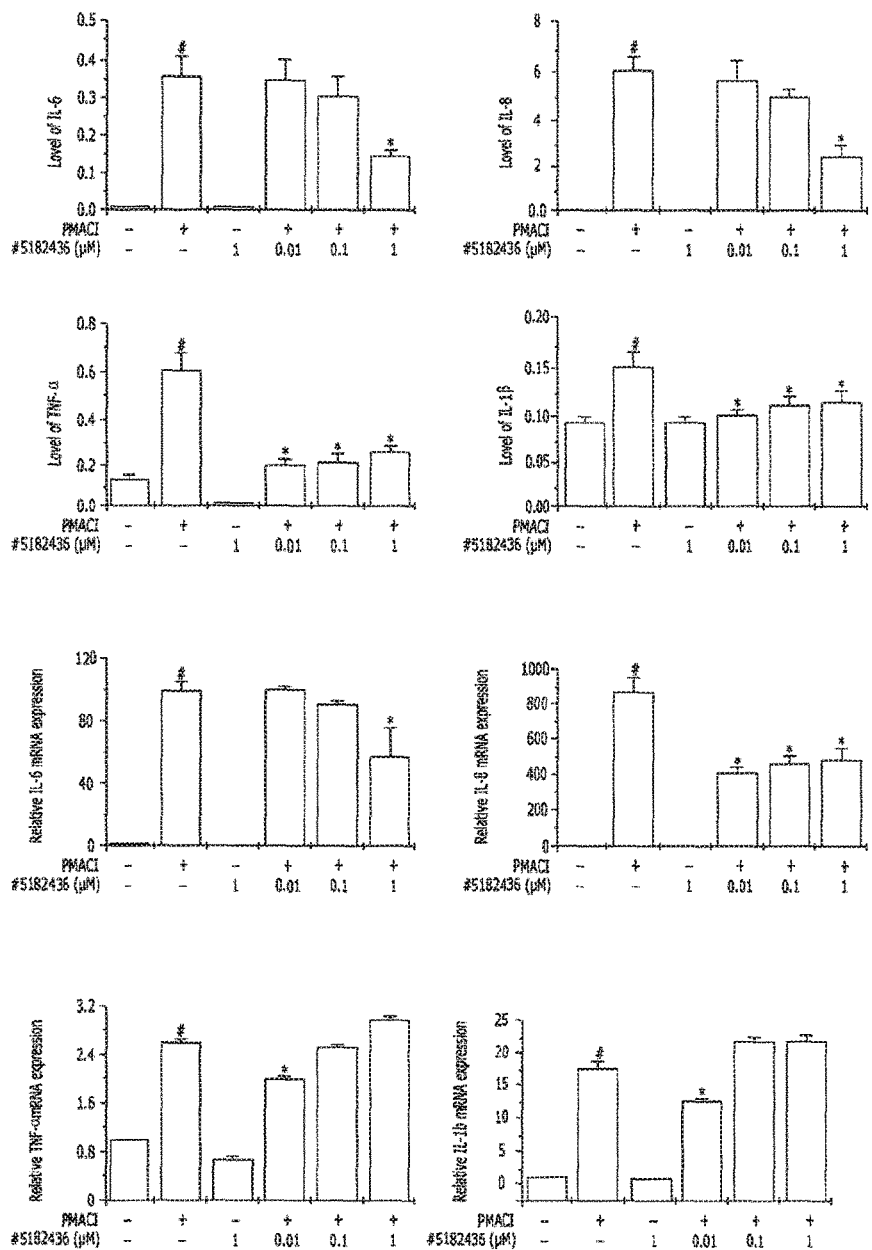
FIG. 7 shows measurement results of inflammatory cytokine mRNA expression in HMC-1 cells.

IPS-07001 (#5182436) significantly inhibited the production and mRNA expression of various inflammatory cytokines (see FIG. 7).

Figure 8:
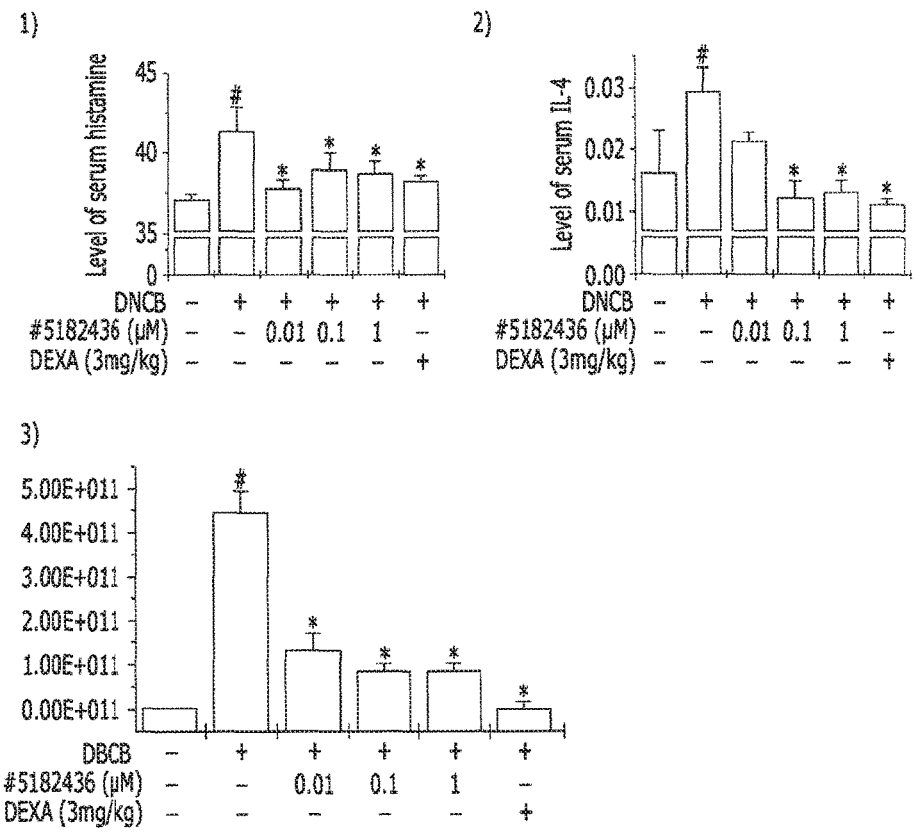
FIG. 8 shows expression measurement results in serum of balb/c mice with DNCB-induced atopic dermatitis.

G. Analysis of Regulatory Effect of IPS-07001 (#5182436) on Histamine, IL-4, and IgE Levels in Serum of DNCB-Applied Balb/c Mice The histamine, IL-4, and IgE levels were measured in DNCB-applied balb/c mice serum. It was found that IPS-07001(#5182436) significantly regulated serum histamine, IL-4, and IgE levels at a concentration of 0.011 μM (see FIG. 8).

Figure 9:
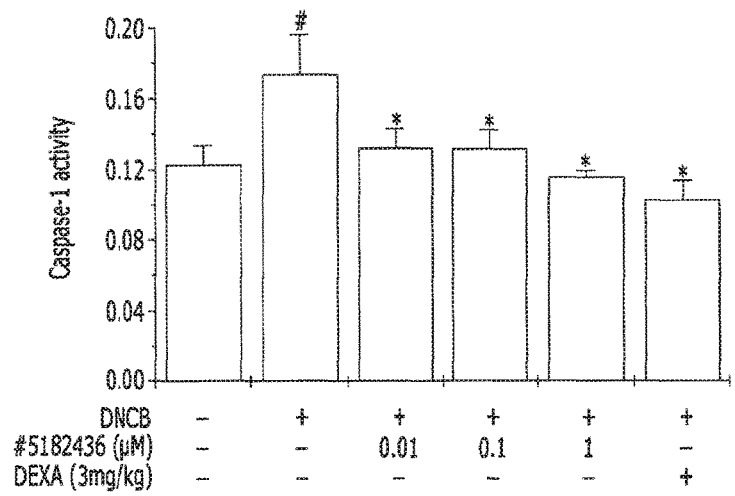
FIG. 9 shows measurement results of caspase-1 activity in balb/c mice dorsal skin with DNCB-induced atopic dermatitis.

H. Analysis of Regulatory Effect of IPS-07001 (#5182436) on Caspase-1 Activity in Dorsal Skin of DNCB-Applied Balb/c Mice In an in vivo atopic dermatitis model, to examine the regulatory effect of IPS-07001 (#5182436) on caspase-1 activity, a caspase-1 assay was conducted using the dorsal skin of DNCB-applied balb/c mice. As a result, it was found that IPS-07001 (#5182436) significantly inhibited caspase-1 activity in a concentration-dependent manner (see FIG. 9).

Figure 10:
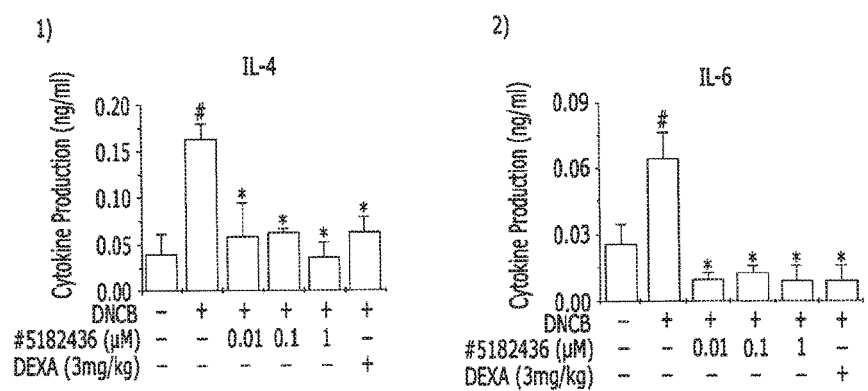
FIG. 10 shows the regulation of inflammatory cytokine in balb/c mice dorsal skin with DNCB-induced atopic dermatitis.

I. Analysis of Regulatory Effect of IPS-07001 (#5182436) on Inflammatory Cytokines in Dorsal Skin of DNCB-Applied Balb/c Mice Inflammatory cytokine levels were analyzed in the dorsal skin of DNCB-applied balb/c mice. It was found that IPS-07001(#5182436) significantly regulated IL-4 and IL-6 levels at a concentration of 0.011 μM (see FIG. 10).

Figure 11:
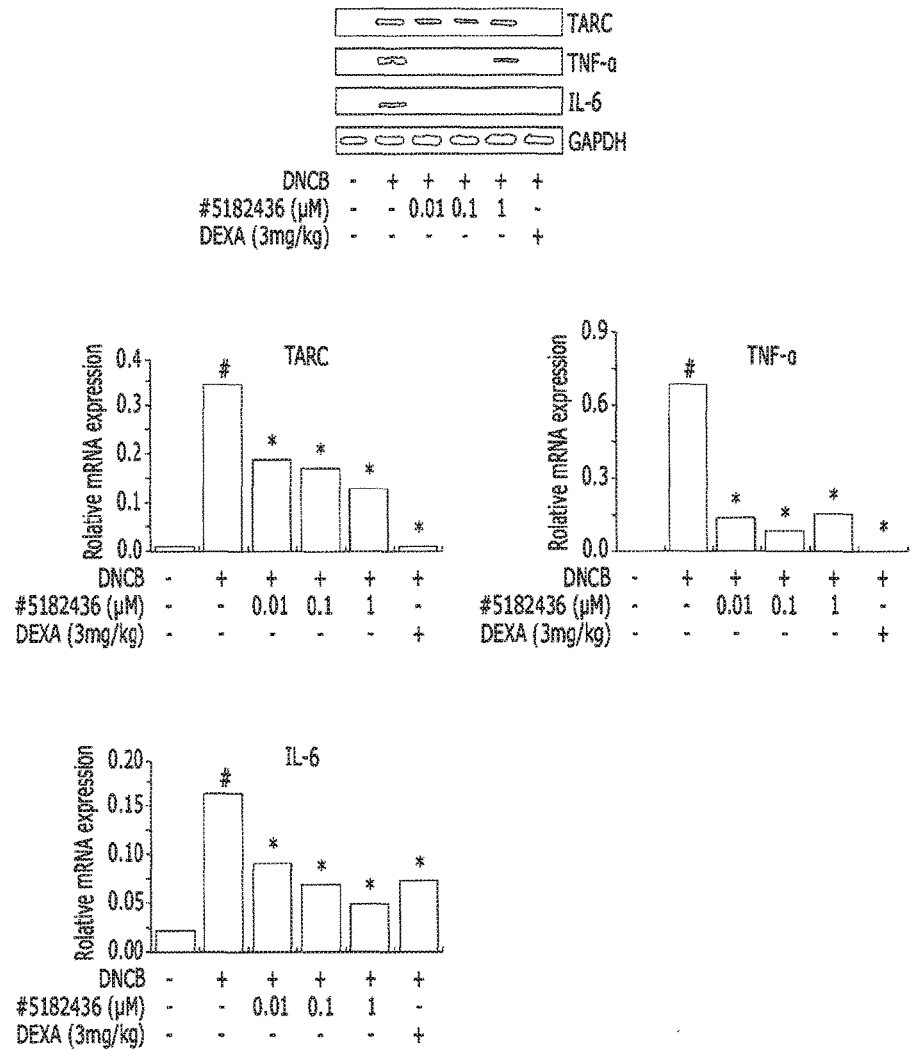
FIG. 11 shows the regulation of inflammatory cytokine in balb/c mice dorsal skin with DNCB-induced atopic dermatitis: 1) RT-PCR electrophoresis results and 2) electrophoresis results measured using a densitometer.

J. Analysis of Regulatory Effect of #5182436 on Inflammatory Cytokine mRNA Expression in Skin Tissue of DNCB-Applied Balb/c Mice As a result of analyzing whether inflammatory cytokine mRNA expression was regulated in skin tissues of DNCB-applied balb/c mice, it was found that IPS-07001(#5182436) regulated TARC, TNF-a, and IL-6 mRNA expression in atopic skin lesions (see FIG. 11).

Figure 12:
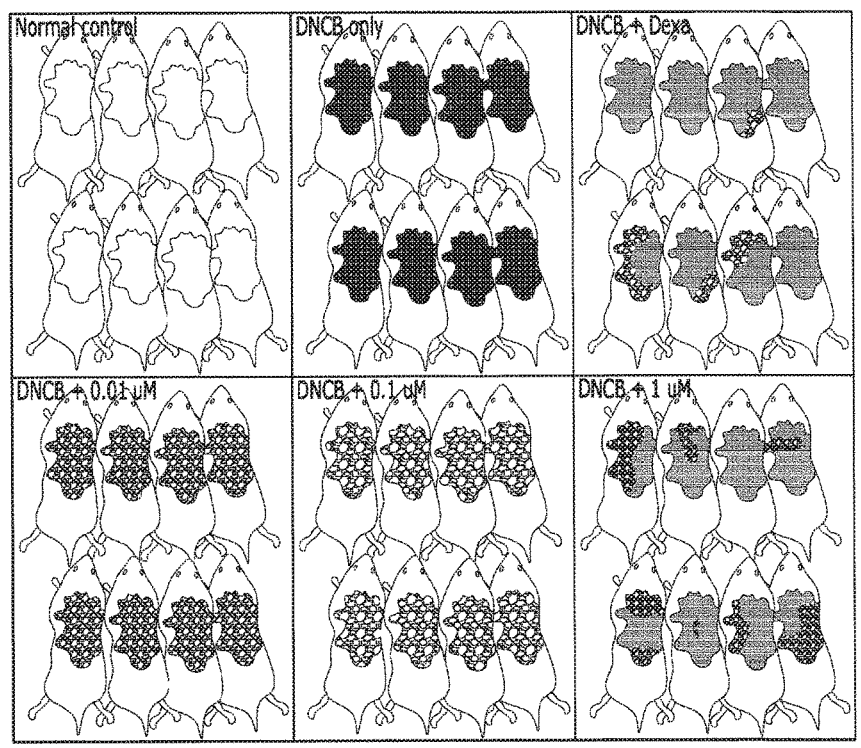
FIG. 12 shows images showing results of treatment of balb/c mice having DNCB-induced atopic dermatitis with IPS-07001 and dexamethasone were treated (0.01 μM, 0.1 μM, and 1 μM, respectively).

Study of Regulatory Effect of DNCB on Atopy-Related Factor in Contact Atopic Dermatitis Animal Model A. Visual Observation Psoriasis and atopic dermatitis are known as representative diseases exhibiting skin dryness. Among these, in particular, atopic dermatitis is a skin disease that is characterized by, in addition to skin dryness, hyperkeratosis, erythema, edema, severe pruritus, exudation, boils, and scabs, and is accompanied by various symptoms such as skin inflammation and the like, e.g., blisters in the acute phase and thickening of the skin in the chronic phase (Bieber T. Atopic dermatitis. N Engl J Med. 2008; 358:1483-94). Accordingly, in the present experiment, skin clinical symptoms were observed mainly with focus on erythema, dry skin, edema & excoriation, erosion, and lichenification. As a result of observation, distinct dryness, erythema, excoriation, and lichenification were observed in a group treated only with DNCB compared to a normal control. In contrast, DNCB-induced skin symptoms except for erythema were mostly eliminated in a dexamethasone-treated group. No significant visual changes were observed at 0.01 μM and 0.1 μM in test material-treated groups, but erythema, excoriation, and lichenification were reduced at 1 μM compared to the DNCB group (see FIG. 12).

B. Epidermal Thickness Change

Figure 13:
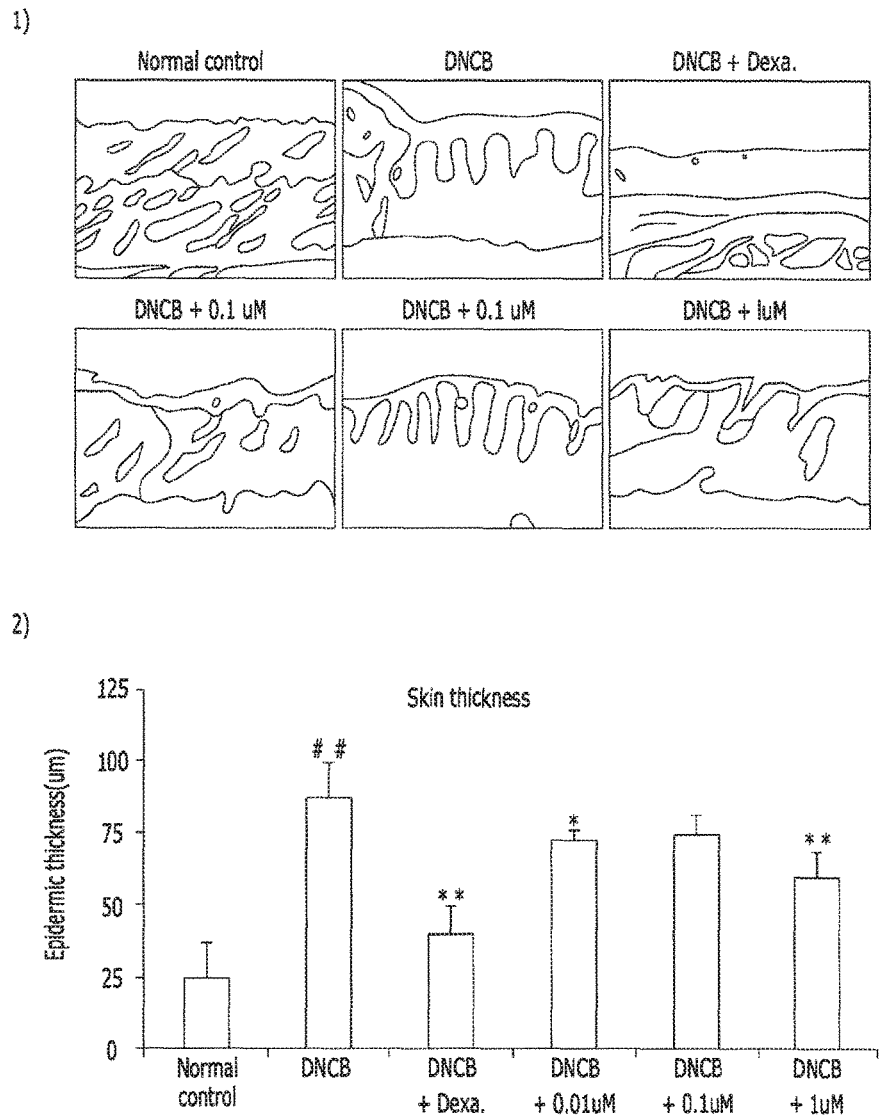
FIG. 13 shows histological characteristics of H&E-stained dorsal skin: 1) measurement results of epidermal thickness values, and 2) for balb/c mice with DNCB-induced atopic dermatitis (epidermal depth) (##$p<0.01$ normal control vs DNCB; *$p<0.01$ DNCB vs treated with 0.01 μM, 0.1 μM, and 1 μM, **$p<0.01$ DNCB vs treated with 0.01 μM, 0.1 μM, and 1 μM, respectively).

In the DNCB group with induced atopy, histological observation showed hyperkeratosis in the skin tissue of the mice. The epidermal thickness of the DNCB group was 87.1±13.0 μm, which was significantly greater than that of the normal control group, i.e., 24.5±10.3 μm, indicating the occurrence of hyperkeratosis, typical of atopic dermatitis. The dexamethasone-treated group as a positive control exhibited an epidermal thickness of 39.9±9.4 μm, indicating a distinct decrease in the thickness of the epidermal layer. In the groups treated with the test material at concentrations of 0.01 μM, 0.1 μM, and 1 μM, the epidermal thickness was decreased to 70.8±4.3 μm, 74.4±7.1 μm, and 60.0±8.2 μm, respectively (see FIG. 13).

C. The Number of Mast Cells in Skin Tissue

Figure 14:
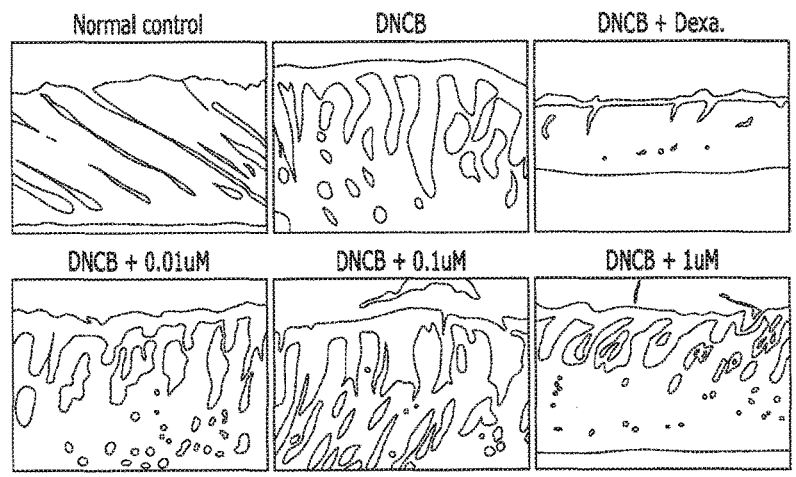
FIG. 14 shows histological characteristics of toluidine blue-stained dorsal skin: 1) images of the stained skin tissues, and 2) measurement results of the amount of mast cells in balb/c mice with DNCB-induced atopic dermatitis disorder (## p<0.01 normal control vs DNCB; ** p<0.01 DNCB vs treated with 0.01 μM, 0.1 μM, and 1 μM, respectively).
Figure 14:
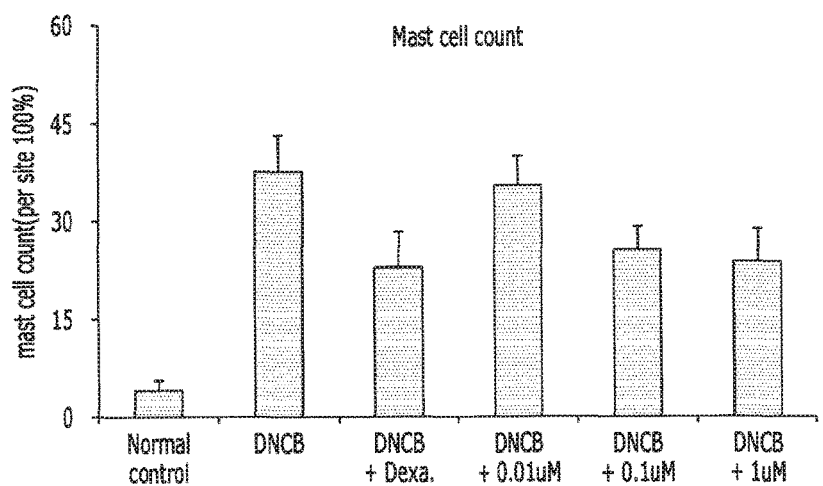

Histamine secreted by the degranulation of mast cells in atopic dermatitis is known to play a major role in the progression of atopic dermatitis by acting as a major cause of pruritus to thereby damage the skin barrier and induce skin inflammation (Lee, E. J., G. E. Ji and M. K. Sung. 2010. Inflamm. Res. 59(10):847-854). After application of the test material for 3 weeks, 0.1 µM test material-applied group (25.8±3.5, p<0.01) and 1 µM test material-applied group (23.8±5.1, p<0.01) showed a statistically significant decrease. These results are similar to those of the DNCB-treated group, which indicates that the test material is effective in alleviating pruritus by reducing the number of mast cells (see FIG. 14).

D. Blood IgE Level

Figure 15:
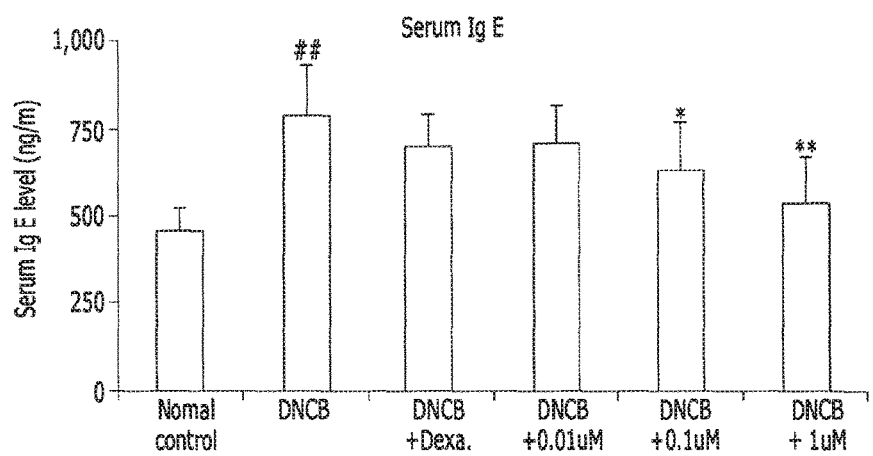
FIG. 15 shows measurement results of IgE in balb/c mice serum with DNCB-induced atopic dermatitis (## p<0.01 normal control vs DNCB; ** p<0.01 DNCB vs treated with 0.01 μM, 0.1 μM, 1 μM, respectively).

The increase in serum IgE is known to be an indicator of atopic dermatitis. In particular, IgE is known to have close correlation with the clinical severity (M. Ban and D. Hetich, Toxicol. Lett, 118, 129 (2001). Atopic dermatitis increases IgE antibody responses (Matsuda, H., Watanabe, N., Geba, G. P., Sperl, J., Tsudzuki, M. and Hiroi, J.: Int. Immunol. 9, 461 (1997). In addition, increased IgE production leads to increased antibody responses and increased IgE-dependent histamine vitreous activity, thereby promoting histamine secretion. Histamine is known to induce the infiltration of eosinophils and to cause acute hypersensitivity and pruritus (H. C. Sung, W. J. Lee, S. J. Lee, and D. W. Kim, Kor. J. Dermatol, 44, 1051 (2006). Thus, a decrease in IgE is considered to be a major indicator of the alleviation of atopic dermatitis. In the present experiment, the DNCB group (790.0±151.8) showed a 70% or higher increase in. IgE level compared to the normal control, whereas the dexamethasone-treated group (703.8±86.5) exhibited a slightly decreased IgE level, but had no statistical significance. In the groups treated with the test material at respective concentrations, a 0.1 µM test material-applied group (632.6±138.8, p<0.05) and a 1 µM test material-applied group (537.9±132.9, p<0.01) exhibited a statistically significant decrease in IgE level (see FIG. 15).

Acute Dermal Toxicity Test

To identify the toxicity pattern and toxicity intensity of IPS-07001, 0 µM and 200 µM single transdermal administration were given to both female and male SD rats, and then the presence or absence of dead and dying animals, clinical symptoms, and body weight changes were observed for 14 days. After observation was completed, the SD rats were autopsied and abnormalities were examined for each individual, thereby obtaining the following results.

A. Mortality

No dead animals were observed in all test material-administered groups during the test period (see Table 7).

TABLE 7

| Dose group (µg/kg bw) | Sex | No. of Animals | Number of death on day |   |   |   |   |   |   |   | 8-14 day | Mortality (%) |
|---|---|---|---|---|---|---|---|---|---|---|---|---|
|   |   |   | 0 | 1 | 2 | 3 | 4 | 5 | 6 | 7 |   |   |
| Test material (0) | Male | 3 | 0 | 0 | 0 | 0 | 0 | 0 | 0 | 0 | 0 | 0/3 (0) |
|   | Female | 3 | 0 | 0 | 0 | 0 | 0 | 0 | 0 | 0 | 0 | 0/3 (0) |
| Test material (200) | Male | 3 | 0 | 0 | 0 | 0 | 0 | 0 | 0 | 0 | 0 | 0/3 (0) |
|   | Female | 3 | 0 | 0 | 0 | 0 | 0 | 0 | 0 | 0 | 0 | 0/3 (0) |

Table 7 shows mortality after treatment with the test material.

B. Clinical Symptoms

After administration of IPS-07001, clinical symptoms including skin lesions were not observed in both male and female rats of groups administered 0 and 200 µM/kg bw (see Table 8). Skin erythema was observed in one rat of each of the 0 µM/kg and 200 µM/kg groups, but this was not considered caused by the test material, and the symptom was eliminated within one day after administration.

TABLE 8

| Dose group (mg/kg bw) | Sex | 30 min to 3 hour | 4 hour | Day 1 | Day 2 | Day 3 | Day 4 | Day 5 | Day 6 | Day 7 | Day 8 | Day 9 | Day 10-14 |
|---|---|---|---|---|---|---|---|---|---|---|---|---|---|
| Test material (0) | Male | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) |
|   | Female | NCS (2/3) Erythema (1/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) |
| Test material (200) | Male | NCS (2/3) Erythema (1/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) |
|   | Female | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) | NCS (3/3) |

Table 8 shows clinical symptoms induced by treatment with the test material.

C. Body Weight Change

All the groups of female and male rats to whom the test material were administered exhibited a decrease in body weight on day 1 after administration. These results are considered attributable to environmental changes in the process of the test material treatment, and a normal body weight increase pattern was shown from day 2.

TABLE 9

| Dose group (mg/kg bw) | Ani. No. | Body weights (g) | | | | | | Weight gain[b] |
|---|---|---|---|---|---|---|---|---|
| | | Day 0[a] | Day 1 | Day 4 | Day 7 | Day 10 | Day 14 | |
| Test material (0) | 1101 | 235.3 | 228.4 | 252.9 | 272 | 292.2 | 314.6 | 79.3 |
| | 1102 | 241.6 | 232.4 | 265.8 | 286.3 | 303.9 | 322.4 | 80.9 |
| | 1103 | 247.3 | 240.5 | 266.1 | 287 | 307.9 | 330.5 | 83.2 |
| | Mean | 241.4 | 233.8 | 261.6 | 281.8 | 301.3 | 322.5 | 81.1 |
| | SD | 6.0 | 6.2 | 7.5 | 8.5 | 8.2 | 8.0 | 2.0 |
| | n | 3 | 3 | 3 | 3 | 3 | 3 | 3 |
| Test material (200) | 1206 | 236 | 227.4 | 256 | 282 | 307.1 | 332.5 | 96.5 |
| | 1207 | 247.1 | 237.9 | 267.5 | 288.8 | 310.5 | 333.1 | 86 |
| | 1208 | 227 | 216.9 | 245.7 | 264 | 281 | 309.4 | 82.4 |
| | Mean | 236.7 | 227.4 | 256.4 | 278.3 | 299.5 | 325.0 | 88.3 |
| | SD | 10.1 | 10.5 | 10.9 | 12.8 | 16.1 | 13.5 | 7.1 |
| | n | 3 | 3 | 3 | 3 | 3 | 3 | 3 |

Table 9 shows body weight changes in male rats treated with the test material.
a): data obtained after 14 hour starvation
b): body weight increases calculated for 0 to 14 days.

TABLE 10

| Dose gyoup (mg/kg bw) | Ani. No | Body weights (g) | | | | | | Weight gain[b] |
|---|---|---|---|---|---|---|---|---|
| | | Day 0[a] | Day 1 | Day 4 | Day 7 | Day 10 | Day 14 | |
| Test material (0) | 2101 | 181.6 | 172.8 | 187.2 | 197.9 | 209.6 | 223 | 41.4 |
| | 2102 | 168.7 | 156.7 | 172 | 181.7 | 188.4 | 194.1 | 25.4 |
| | 2103 | 182.1 | 170.3 | 188.5 | 202 | 208.2 | 223.3 | 41.2 |
| | Mean | 177.5 | 166.6 | 182.6 | 193.9 | 202.1 | 213.5 | 36.0 |
| | SD | 7.6 | 8.7 | 9.2 | 10.7 | 11.9 | 16.8 | 9.2 |
| | n | 3 | 3 | 3 | 3 | 3 | 3 | 3 |
| Test material (200) | 2206 | 178.8 | 165.6 | 187.3 | 193.2 | 197 | 205.6 | 26.8 |
| | 2207 | 175.8 | 159 | 181.1 | 191.5 | 204.4 | 212.6 | 36.8 |
| | 2208 | 182.1 | 175.3 | 194.2 | 209 | 227.6 | 236.3 | 54.2 |
| | Mean | 78.9 | 166.6 | 187.5 | 197.9 | 209.7 | 218.2 | 39.3 |
| | SD | 3.2 | 8.2 | 6.6 | 9.7 | 16.0 | 16.1 | 13.9 |
| | n | 3 | 3 | 3 | 3 | 3 | 3 | 3 |

Table 10 shows body weight changes in female rats treated with the test material
a): data obtained after 14 hour starvation
b): body weight increases calculated for 0 to 14 days.

D. Autopsy Findings

After completion of the observation period, visual pathological examination was performed on surviving animals and no individual showed any abnormalities (see Table 11).

TABLE 11

| Dose group (mg/kg bw) | Sex | No. of animal examined | Gross findings (internal and external) |
|---|---|---|---|
| Test material (0) | Male | 3 | NGF [a] |
| | Female | 3 | NGF [a] |

TABLE 11-continued

| Dose group (mg/kg bw) | Sex | No. of animal examined | Gross findings (internal and external) |
|---|---|---|---|
| Test material (200) | Male | 3 | NGF [a] |
| | Female | 3 | NGF [a] |

Table 11 shows autopsy findings in test material-treated rats
NGF: No abnormal findings
a): Observed in surviving animals on day 15

E. Lethal Dose

The lethal dose (LD50) by transdermal administration of the test material was 200 μM/kg/4 ml bw or more in both female and male rats.

Establishment of Antibody Microarray System to Identify Mechanism

A. Cytokine & Chemokine Antibody Microarray Protein Chip

Figure 2:
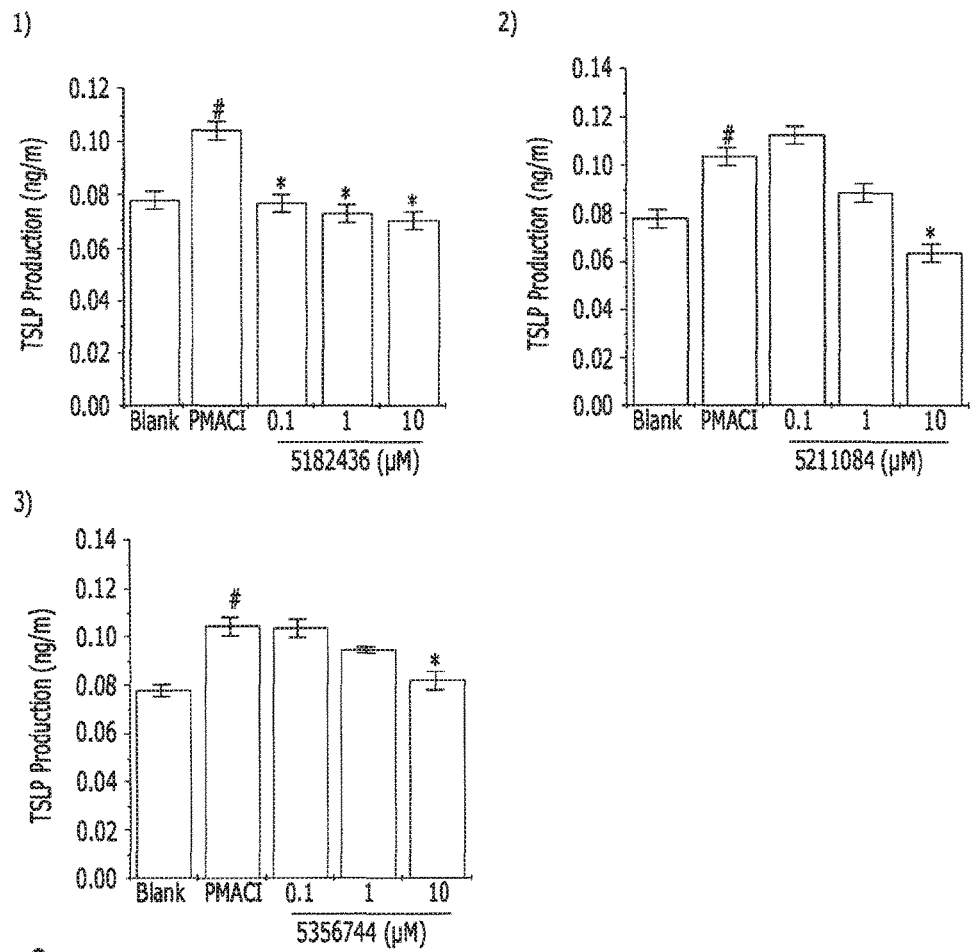
FIG. 2 shows measurement results of the amount of TSLP in human mast cells (HMC-1 cells).
Figure 16:
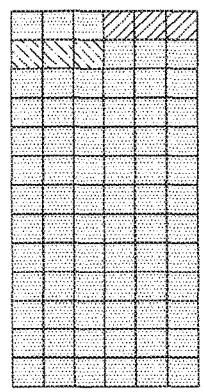
FIG. 16 shows analysis of cytokine & chemokine antibody microarray protein chips, wherein in 1), Control denotes a skin tissue sample treated only with 1% DNCB, ISP-07001 denotes a skin tissue sample treated with 1% DNCB and 1 μM IPS-07001, and in an INR fluorescence image, red color means increased expression, green color means decreased expression, and black color means no difference in expression; and 2) INR values of 1.1 or higher indicate increased expression, and INR values of 0.9 or less indicate decreased expression.
Figure 16:
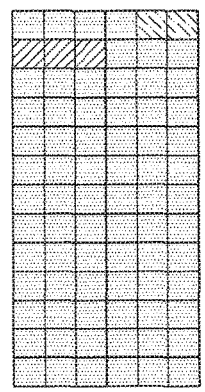
Figure 16:
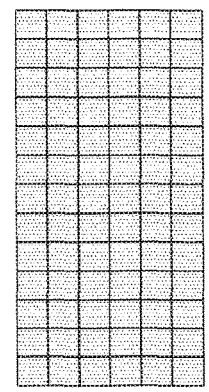
Figure 16:
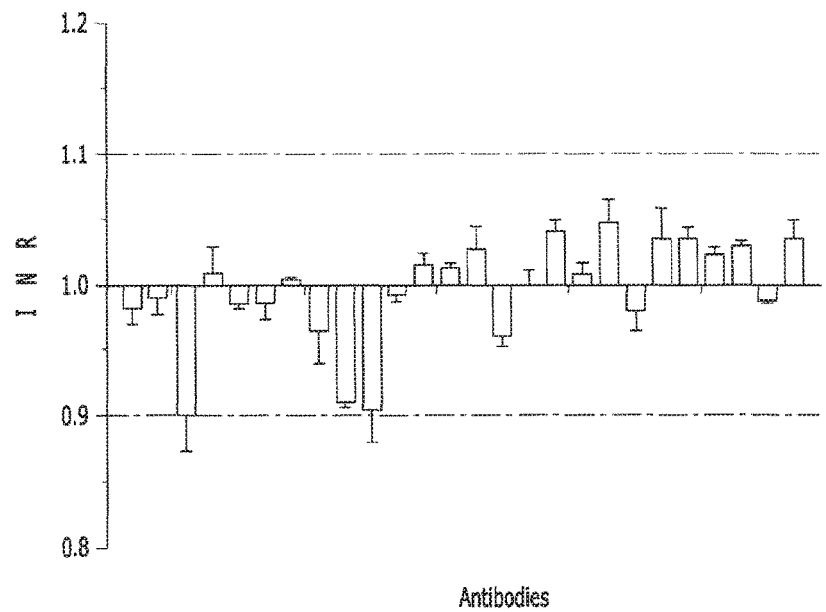

Tissue lysateS obtained by disrupting each of the skin tissue treated only with DNCB and the skin tissue treated with DNCB and IPS-07001 was labeled with a fluorescent material (Cy3 or Cy5), and protein expression profiling was conducted using an antibody chip. Antibody microarray protein chip analysis was performed with reference to an antibody map immobilized on ProteoChip. Fluorescence images obtained by comparing expression levels on 26 antibody-immobilized antibody chips are shown in FIG. 16-1. A graph for the INR analysis results is shown in FIG. 16-2.

As a result of the antibody chip-based profiling, the skin tissue samples did not exceed the range of 1±0.1 as a threshold for determining increase/decrease, but a decrease in the expression of three types of cytokine proteins, IL-6, IL-22, and IL-33, whose level reached most closely to the threshold, was found in the skin tissue samples.

IL-6, secreted from Th2 cells has been reported to be increased in T cells of patients with atopic dermatitis (Toshitani, Akito, et al. J Invest Dermatol 100.3 (1993): 299-304). IL-22, produced in Th17 cells, is known to contribute to the development of inflammatory skin diseases and play a key role in inflammatory diseases. In addition, it has been reported that IL-22 expression was increased in atopic dermatitis (Cho, Kyung-Ah, et al. International immunology 24.3 (2012): 147-158). IL-33, a recently known cytokine belonging to the IL-1 family, is associated with a Th2-type immune response, and is expressed in cells of barrier tissues. However, its role in allergic skin inflammation is not known well, but it is strongly suggested to be related to atopic dermatitis. According to the recent studies, it has been reported that the expression of IL-33 is increased in induced atopic dermatitis (Savinko, Terhi, et al. Journal of Investigative Dermatology 132.5 (2012): 1392-1400).

It has been reported that expressions of IL-6, IL-22 and IL-33 expression increased in atopic dermatitis skin, and these are closely related, with the progression of atopic dermatitis. In the present invention, the above three cytokines are considered to be reduced due to the alleviation of atopic dermatitis symptoms.

B. Western Blotting Analysis

Tissue lysates obtained by disrupting DNCB only-treated skin tissue and DNCB- and IPS-07001-treated skin tissue were subjected to SDS-PAGE and then transferred to PVDF membranes, and expression levels of particular proteins were examined using specifically binding antibodies.

Figure 17:
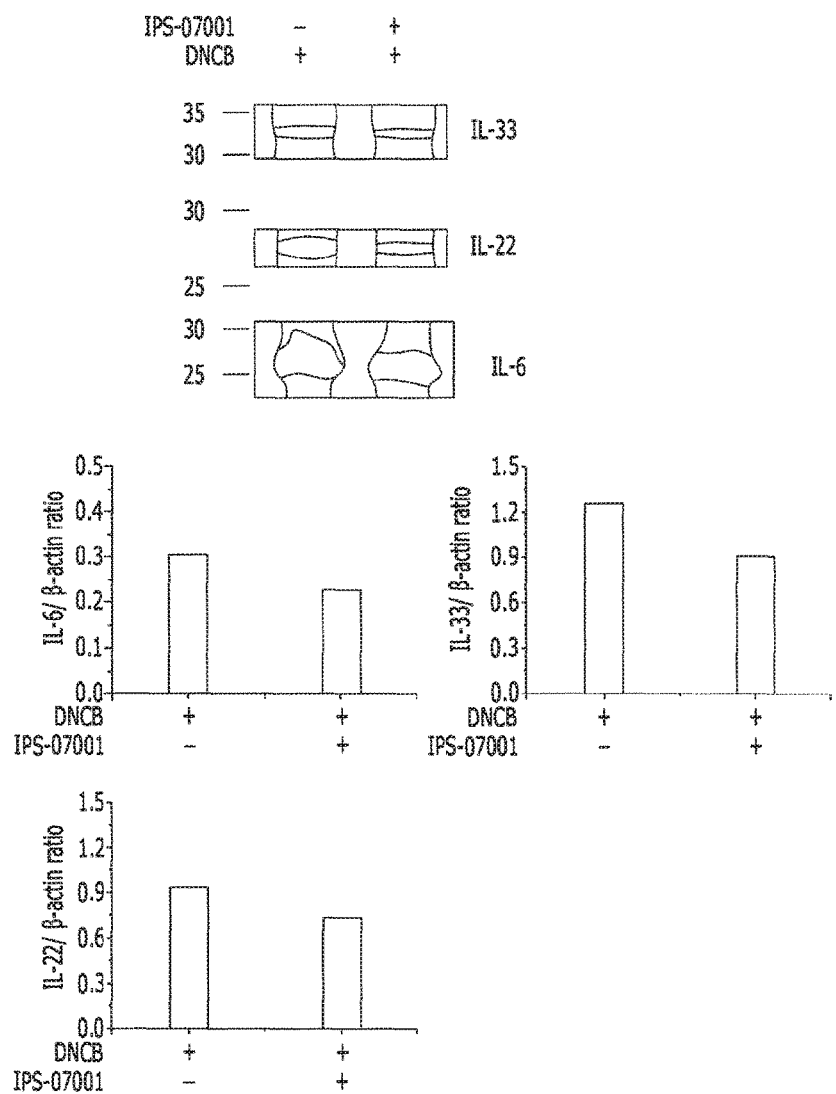
FIG. 17 shows changes in the expression of cytokine proteins in balb/c mice dorsal skin with DNCB-induced atopic dermatitis: 1) western blotting images, and 2) graphs showing measurement results of the intensity of bands.
Figure 18:
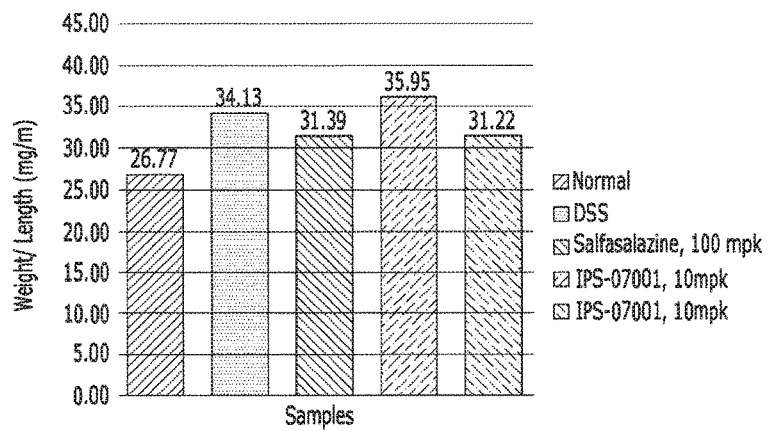
FIG. 18 shows an inhibitory effect of IPS-07001 (Formula 1) on acute inflammatory bowel disease (IBD) in a DSS-induced animal model.
Figure 19:
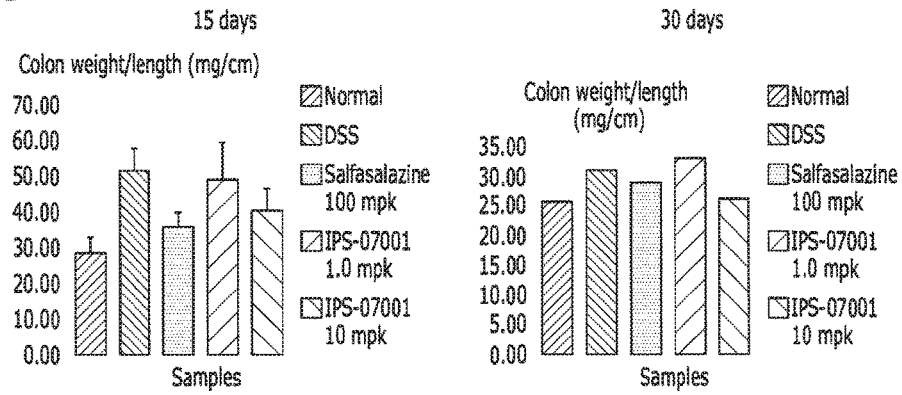
FIG. 19 shows an inhibitory effect of IPS-07001 (Formula 1) on chronic IBD in a DSS-induced animal model.

As a result, the skin tissue samples did not exceed the range of 1±0.1 as a threshold for determining increase/decrease in antibody microarray protein chip results, but western blotting on the three cytokines, IL-6, IL-22, and IL-33 reaching most closely to the threshold, found that the level of protein expression changed slightly, but was decreased (see FIG. 17).

Example 6

IPS-07004 (Formula 4) and Atopic Dermatitis

IPS-07004 was found from literature search for a compound having a structure similar to that of 07001, following screening of 07001 (Formula 1), and purchased from Key Organics (London, UK).

(1) Cell culture: A human skin cell line (HaCat cells) was cultured in RPMI containing 10% FBS at 37° C. and 5% $CO_2$. Candidate materials were dissolved in DMSO, and then filtered using a 0.22 μm filter. The resulting candidate materials were diluted with DMSO and the HaCat cells were treated therewith.

(2) Cytotoxicity (MTT-assay): After stabilizing HaCat cells ($3\times10^5$ cells/ml) for 1 hour, they were treated with candidate materials variously beginning from a concentration of 10 μM, followed by treatment with Poly (I:C) for 8 hours. Then, the medium was replaced by a fresh medium, 5 mg/ml of an MTT solution was then added thereto, and the mast cells were incubated at 37° C. for 4 hours. 250 DMSO was added to the HaCat cells, MTT formazan was extracted therefrom, and absorbance of each well was measured at 540 nm using an ELISA reader.

(3) Caspase-1 Activity Analysis:

Recombinant caspase-1 and a drug were allowed to react, and then activity was measured using a caspase-1 assay kit (R&D Systems Inc., Minneapolis, Minn., USA).

Example 7

Inflammatory Bowel Disease

Experimental Animal

Six-week-old female SPF (Specific pathogen-free) C57BL/6 mice were purchased from DuPont Biotech. The mice were allowed to freely ingest a feed and water after an acclimation period of 1 week in an animal room of Hoseo University Safety Evaluation Center maintained at temperature of 21±3° C., humidity of 50±20%, and light/darkness cycle of 12 h/12 h. All procedures in the present animal experiment were conducted after approved by the Animal Experimental Ethics Committee of Hoseo University (HTRC-15-19, and HTRC-16-22(2)).

Group Division and Induction of Enteritis

Dextran sodium sulfate (cat no 160110 by Mpbio. corn) as a colitis inducer was diluted to 3% concentration in drinking water and orally administered to mice to induce enteritis. The mice were divided into 6 groups and DW was administered to the animals of a control, and 1.0 mg/kg and 10 mg/kg of the test material were orally administered to the animals of the experimental groups once a day for 5 weeks. Sulfasalazine (100 mg/kg) dissolved in crude olive oil was orally administered once a day to the animals of a positive control. In acute cases, disease progression levels were examined after 5 days of administration. In chronic cases, disease progression levels were examined 15 days and 30 days after the 5 days of administration (reference: Toxicology Reports 2 (2015) 10391045-Caryophyllene attenuates dextran sulfate sodium-induced colitis in mice via modulation of gene expression associated mainly with colon inflammation).

Body Weight Measurement and Feces Observation

Body weights were measured once for 5 days or more during the test period. The measured weights were quantified as 0 point if there was no difference compared with the normal control, 1 point for weight loss rate of 15%, 2 points for 510%, 3 points for 1015%, and 4 points for >15%. Feces observation was performed to examine the incidence of diarrhea, and the results thereof were quantified as scores (0, normal stool; 1, mildly soft stool; 2, very soft stool; 3, very soft stool (no regular shape); 4, watery stool).

Collection of Tissue and Blood Samples

Rectal tissues and blood were collected from 5 individuals for each of the autopsy times. Yuhan ketamine 50® (Yuhan Corporation, Korean) and Rompun (Bayer, USA) were mixed in a ratio of 3:1, and then used to anesthetize animals via muscular injection. Each anesthetized animal was subjected to laparotomy to collect blood from the abdominal artery, and after blood collection, the abdominal artery was cut and subjected to venesection and death to collect rectal tissue. The length and weight of the collected tissue were measured to calculate weight per 1 cm of the tissue. Some of the collected tissues were used in biopsy, and some thereof were frozen in liquid nitrogen and stored at −70° C. before analysis.

Histological Examination

For histologic evaluation, some tissues of the rectum were fixed in 4% neutral buffered formalin (4% NBF), followed by general histological examination, and then were microsectioned to a thickness of 4 μm using a microtome and haematoxylin & eosin staining was performed thereon. The degree of inflammation was divided into five stages (normal—0, minimal—1, mild—2, moderate—3, and severe—4) based on observation under an optical microscope.

Results of the above example will be described below.

Atopy Inhibitory Effect of IPS-07004

Figure 22:
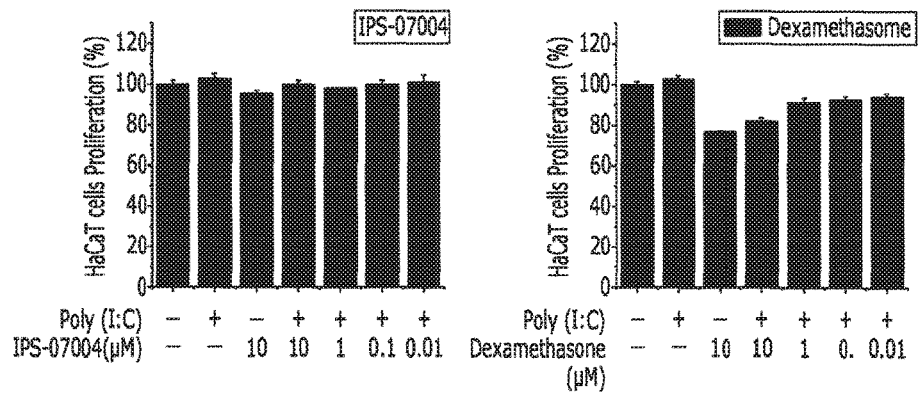
FIG. 22 shows an effect of IPS-07004 (Formula 4) on HaCat cell proliferation.
Figure 23:
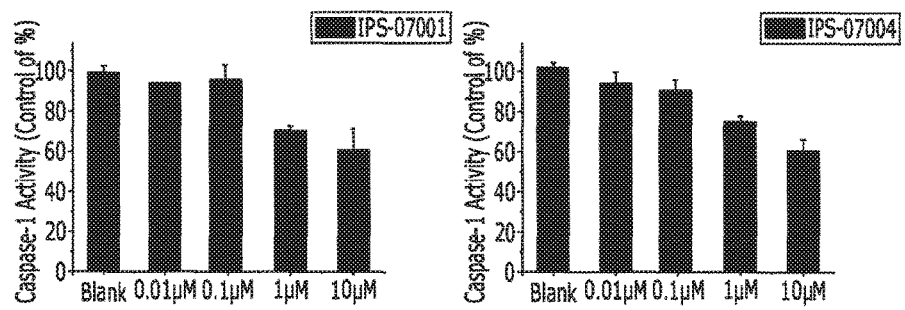
FIG. 23 shows inhibitory effects of IPS-07001 (Formula 1) and IPS-07004 (Formula 4) on human recombinant caspase-1 activity.
Figure 24:
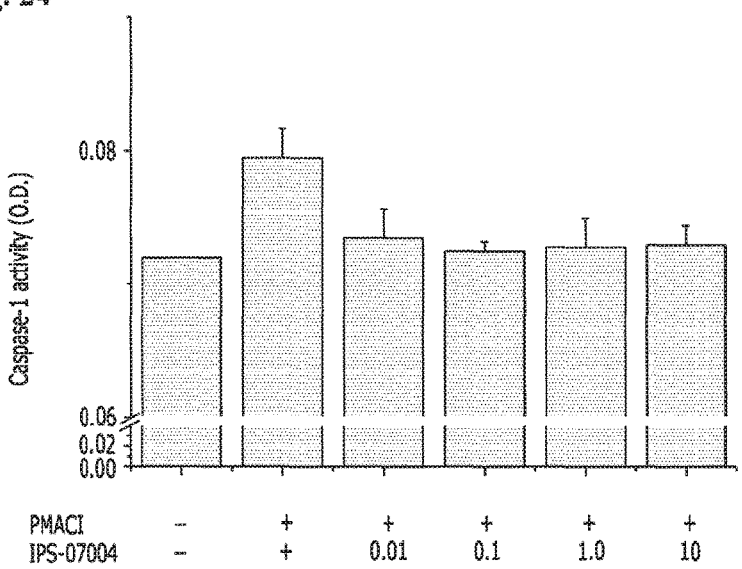
FIG. 24 shows an effect of IPS-07004 (Formula 4) on human caspase-1 activity in HMC-1 cells.
Figure 25:
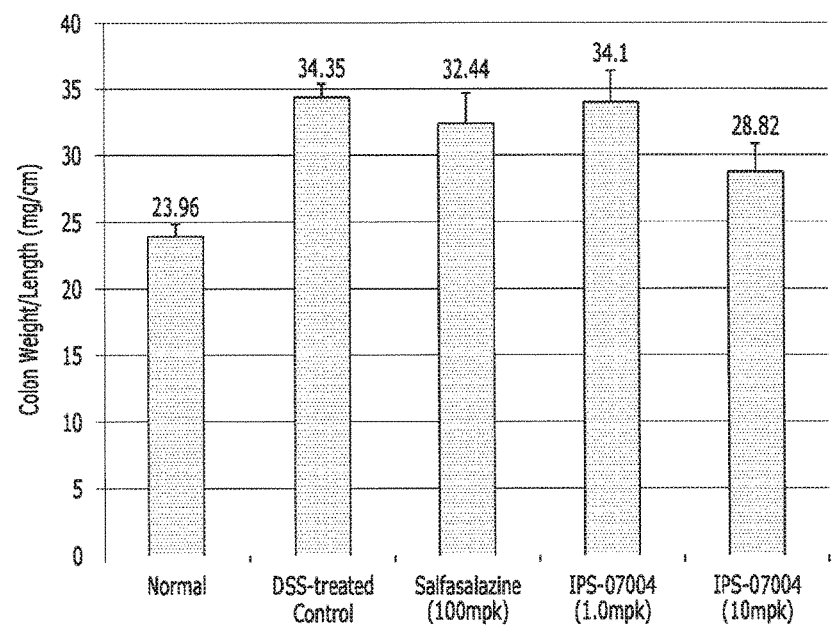
FIG. 25 shows an inhibitory effect of IPS-07004 (Formula 4) on acute IBD in a DSS-induced animal model.

In the case of IPS-07004, no cytotoxicity was observed in the HaCat cell-based assay, and it was found that the compound inhibits both recombinant caspase-1 activity and caspase-1 activity in HMC-1 cells, thereby inhibiting atopy (see FIGS. 22 to 24).

IBD Enteritis Inhibitory Effect of IPS-07001 (Formula 1) and IPS-07004 (Formula 4)

Figure 20:
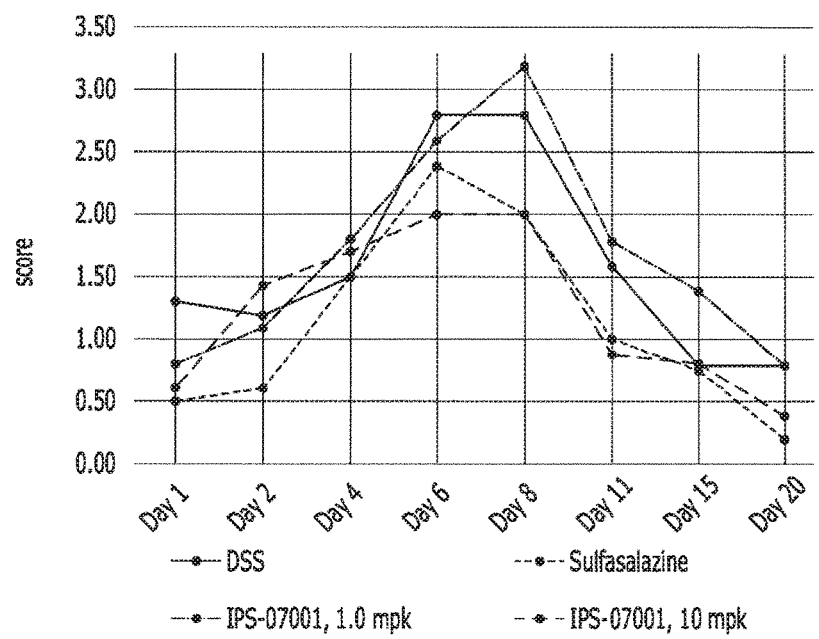
FIG. 20 shows an effect of IPS-07001 (Formula 1) on diarrhea scores in a DSS-induced animal model.
Figure 21:
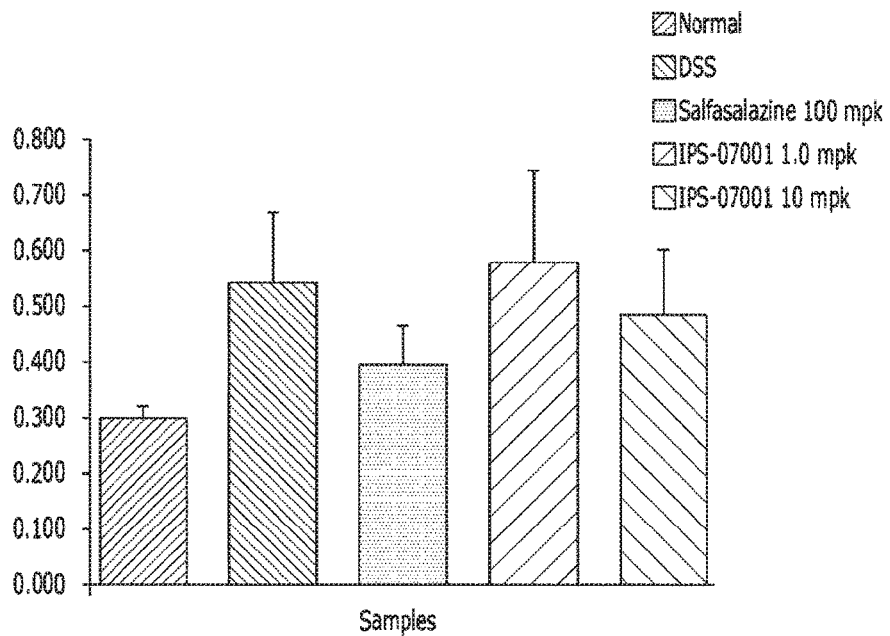
FIG. 21 shows an inhibitory effect of IPS-07001 (Formula 1) on splenic weights in a DSS-induced animal model.
Figure 26:
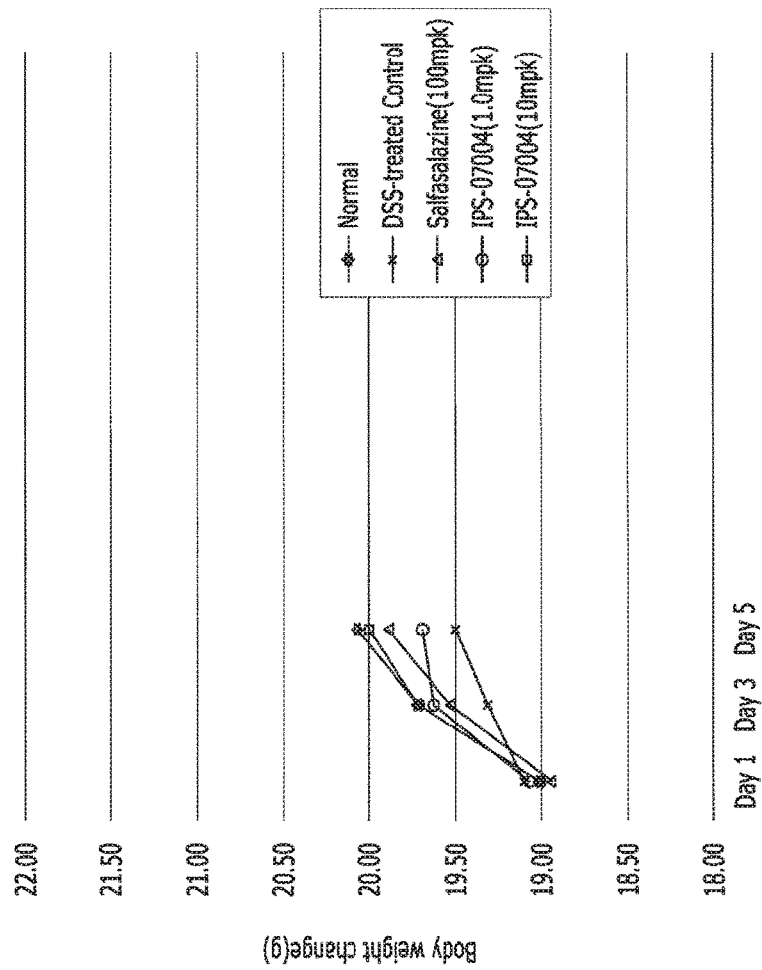
FIG. 26 shows an inhibitory effect of IPS-07004 (Formula 4) on body weight changes in a DSS-induced animal model.
Figure 27:
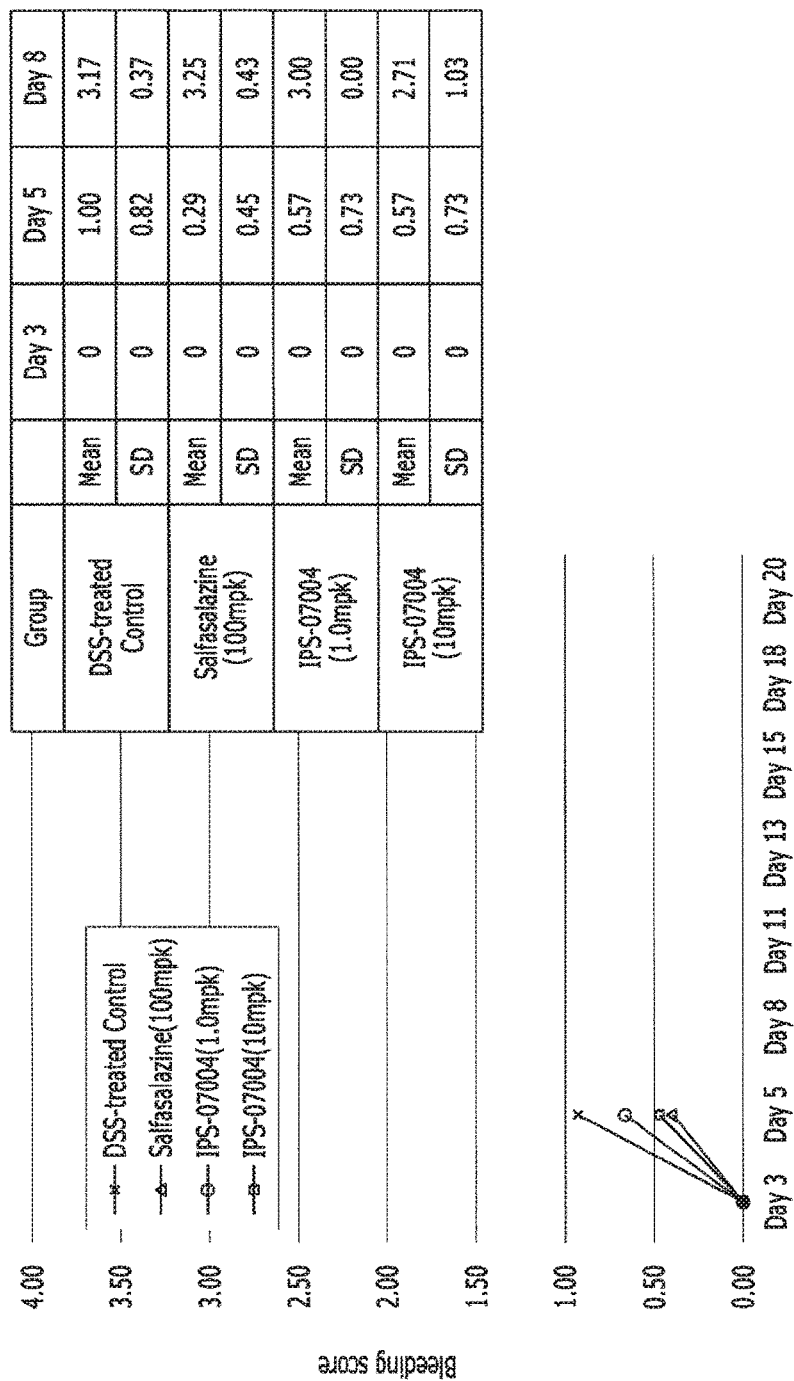
FIG. 27 shows an inhibitory effect of IPS-07004 (Formula 4) on bleeding scores in a DSS-induced animal model.
Figure 28:
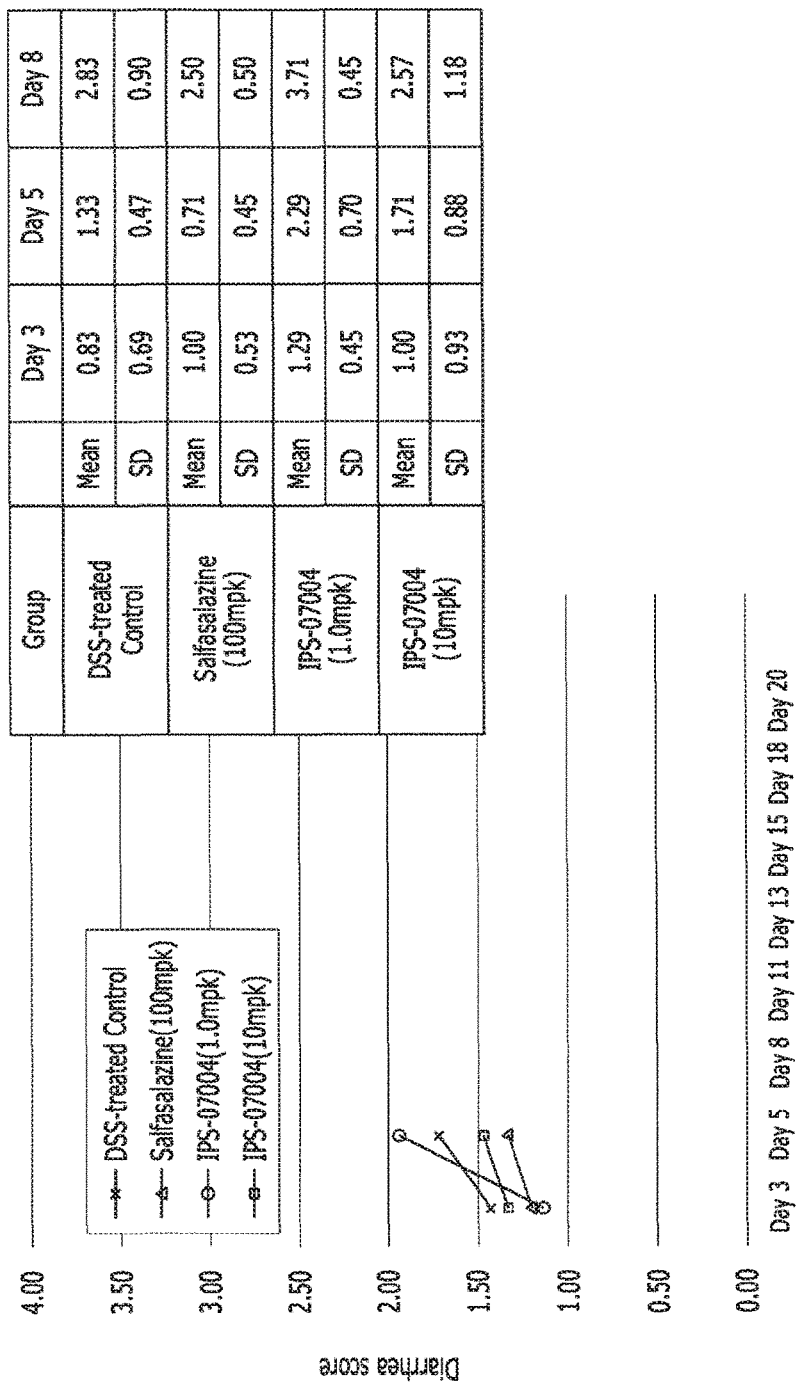
FIG. 28 shows an inhibitory effect of IPS-07004 (Formula 4) on diarrhea scores in a DSS-induced animal model.

The inhibitory effects of IPS-07001 and IPS-07004 on enteritis were observed using the DSS-induced animal model constructed by the above experimental method. The doses were divided into 1.0 mg/kg and 10 mg/kg, and oral administration was performed. Efficacies were analyzed by a ratio of enteric weight to enteric length (wt/cm), and further analyzed by weight change, diarrhea, melena, and the like. As a result of experimentation, the two substances were found to show superior enteritis inhibitory activity at a dose of 10 mg/kg compared to a DSS control (see FIGS. 18 to 20, 25, 27 and 28). Weight change was similar to that of the normal group, and it was observed that melena was significantly decreased compared to the DSS-induced group (see FIGS. 20, 26, and 27). It is believed that this enteritis inhibitory mechanism controls an inflammation-inducing mechanism by inhibiting caspase-1, a key protein of inflammasomes.

The invention claimed is:

1. A method of treating atopic dermatitis in a patient in need thereof, comprising administering to the patient about 50 mg to about 500 mg of proguanil (Formula 4), or a pharmaceutically acceptable salt thereof

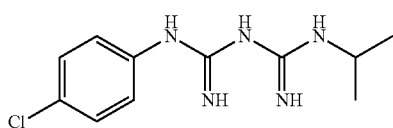

(Formula 4)

2. The method of claim 1, comprising administering to the patient about 75 mg to about 350 mg of proguanil, or a pharmaceutically acceptable salt thereof.

3. The method of claim 1, wherein the proguanil or pharmaceutically acceptable salt thereof is administered orally.

4. A method of treating inflammatory bowel disease in a patient in need thereof, comprising administering to the patient about 50 mg to about 500 mg of proguanil (Formula 4), or a pharmaceutically acceptable salt thereof

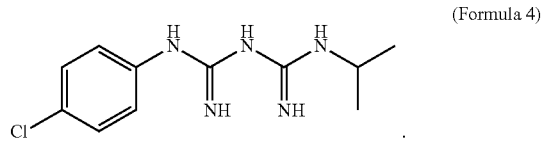 [SMILES: CC(C)NC(=N)NC(=N)Nc1ccc(Cl)cc1]

(Formula 4)

5. The method of claim 4, comprising administering to the patient about 75 mg to about 350 mg of proguanil, or a pharmaceutically acceptable salt thereof.

6. The method of claim 4, wherein the proguanil or pharmaceutically acceptable salt thereof is administered orally.

7. The method of claim 4, wherein the inflammatory bowel disease is ulcerative colitis.

8. The method of claim 4, wherein the inflammatory bowel disease is Crohn's disease.

9. A method of inhibiting caspase-1 activity in a patient in need thereof, comprising administering to the patient proguanil (Formula 4), or a pharmaceutically acceptable salt thereof

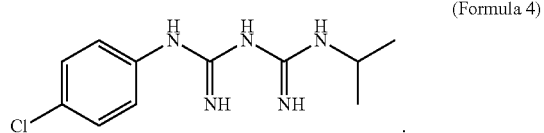 [SMILES: CC(C)NC(=N)NC(=N)Nc1ccc(Cl)cc1]

(Formula 4)

10. The method of claim 9, wherein the patient suffers from atopic dermatitis or inflammatory bowel disease.

11. The method of claim 9, wherein the proguanil or pharmaceutically acceptable salt thereof is administered in an amount of about 50 mg to about 500 mg.

12. The method of claim 9, wherein the proguanil or pharmaceutically acceptable salt thereof is administered orally.

* * * * *